United States Patent
Schenck et al.

(10) Patent No.: US 9,381,288 B2
(45) Date of Patent: Jul. 5, 2016

(54) FLUID HANDLING SYSTEM

(71) Applicant: THORATEC CORPORATION, Pleasanton, CA (US)

(72) Inventors: Alan Schenck, Sunnyvale, CA (US); Michael L. Green, Pleasanton, CA (US); Keif M. Fitzgerald, San Jose, CA (US); Paul F. Muller, San Carlos, CA (US); Joseph P. Sullivan, Issaquah, WA (US); Keith Schubert, Redmond, WA (US); Peter W. Bristol, Seattle, WA (US); Jeffrey Paul Mills, Barrington, IL (US); Paul C. Leonard, Woodinville, WA (US); Richard L. Keenan, Livermore, CA (US)

(73) Assignee: THORATEC CORPORATION, Pleasanton, CA (US)

( * ) Notice: Subject to any disclaimer, the term of this patent is extended or adjusted under 35 U.S.C. 154(b) by 0 days.

(21) Appl. No.: 14/203,978

(22) Filed: Mar. 11, 2014

(65) Prior Publication Data
US 2014/0275725 A1 Sep. 18, 2014

Related U.S. Application Data

(60) Provisional application No. 61/780,656, filed on Mar. 13, 2013.

(51) Int. Cl.
*A61M 1/10* (2006.01)
*A61M 1/12* (2006.01)
(Continued)

(52) U.S. Cl.
CPC ............ *A61M 1/125* (2014.02); *A61M 1/1024* (2014.02); *A61M 1/1034* (2014.02); *A61M 1/122* (2014.02); *A61M 1/3659* (2014.02); *A61M 5/142* (2013.01); *A61M 5/172* (2013.01)

(58) Field of Classification Search
CPC . A61M 25/0122; A61M 25/00; A61M 1/101; A61M 1/125
See application file for complete search history.

(56) References Cited

U.S. PATENT DOCUMENTS

| | | |
|---|---|---|
| 1,902,418 A | 3/1933 | Pilgrim |
| 2,356,659 A | 10/1942 | Aguiar |

(Continued)

FOREIGN PATENT DOCUMENTS

| | | |
|---|---|---|
| CA | 2701810 | 4/2009 |
| CN | 101820933 | 9/2010 |

(Continued)

OTHER PUBLICATIONS

ABIOMED, "Impella 5.0 with the Impella Console, Circulatory Support System, Instructions for Use & Clinical Reference Manual," Jun. 2010, in 122 pages.

(Continued)

*Primary Examiner* — Theodore Stigell
*Assistant Examiner* — Michael D Abreu
(74) *Attorney, Agent, or Firm* — Knobbe, Martens, Olson & Bear LLP

(57) ABSTRACT

Various embodiments of a fluid handling system are disclosed herein. For example, the fluid handling system can include a catheter assembly and a console configured to control the operation of the catheter assembly. A removable interface member can be configured to provide fluid and electrical communication between the catheter assembly and the console.

27 Claims, 9 Drawing Sheets

(51) Int. Cl.
　　*A61M 1/36*　　　　(2006.01)
　　*A61M 5/142*　　　(2006.01)
　　*A61M 5/172*　　　(2006.01)

(56) References Cited

U.S. PATENT DOCUMENTS

| | | | |
|---|---|---|---|
| 2,649,052 A | 8/1953 | Weyer |
| 2,664,050 A | 12/1953 | Abresch |
| 2,684,035 A | 7/1954 | Kemp |
| 2,789,511 A | 4/1957 | Warren |
| 2,896,926 A | 7/1959 | Chapman |
| 2,935,068 A | 5/1960 | Donaldson |
| 3,080,824 A | 3/1963 | Boyd et al. |
| 3,455,540 A | 7/1969 | Marcmann |
| 3,510,229 A | 5/1970 | Smith |
| 3,812,812 A | 5/1974 | Hurwitz |
| 3,860,968 A | 1/1975 | Shapiro |
| 3,904,901 A | 9/1975 | Renard et al. |
| 3,995,617 A | 12/1976 | Watkins et al. |
| 4,115,040 A | 9/1978 | Knorr |
| 4,129,129 A | 12/1978 | Amrine |
| 4,135,253 A | 1/1979 | Reich et al. |
| 4,143,425 A | 3/1979 | Runge |
| 4,149,535 A | 4/1979 | Volder |
| 4,304,524 A | 12/1981 | Coxon et al. |
| D264,134 S | 4/1982 | Xanthopoulos |
| 4,382,199 A | 5/1983 | Isaacson |
| 4,392,836 A | 7/1983 | Sugawara |
| 4,458,366 A | 7/1984 | MacGregor |
| 4,537,561 A | 8/1985 | Xanthopoulos |
| 4,540,402 A | 9/1985 | Aigner |
| 4,560,375 A | 12/1985 | Schulte et al. |
| 4,589,822 A | 5/1986 | Clausen et al. |
| 4,625,712 A | 12/1986 | Wampler |
| 4,655,745 A | 4/1987 | Corbett |
| 4,673,334 A | 6/1987 | Allington et al. |
| 4,686,982 A | 8/1987 | Nash |
| 4,704,121 A | 11/1987 | Moise |
| 4,728,319 A | 3/1988 | Masch |
| 4,753,221 A | 6/1988 | Kensey et al. |
| 4,769,006 A | 9/1988 | Papantonakos |
| 4,817,586 A | 4/1989 | Wampler |
| 4,846,152 A | 7/1989 | Wampler et al. |
| 4,895,557 A | 1/1990 | Moise et al. |
| 4,900,227 A | 2/1990 | Trouplin |
| 4,902,272 A | 2/1990 | Milder et al. |
| 4,906,229 A | 3/1990 | Wampler |
| 4,908,012 A | 3/1990 | Moise et al. |
| 4,919,647 A | 4/1990 | Nash |
| 4,944,722 A | 7/1990 | Carriker et al. |
| 4,955,856 A | 9/1990 | Phillips |
| 4,957,504 A | 9/1990 | Chardack |
| 4,964,864 A | 10/1990 | Summers et al. |
| 4,969,865 A | 11/1990 | Hwang et al. |
| 4,976,270 A | 12/1990 | Parl et al. |
| 4,985,014 A | 1/1991 | Orejola |
| 4,994,017 A | 2/1991 | Yozu |
| 4,995,857 A | 2/1991 | Arnold |
| 5,000,177 A | 3/1991 | Hoffman et al. |
| 5,021,048 A | 6/1991 | Buckholtz |
| 5,044,902 A | 9/1991 | Malbec |
| 5,045,072 A | 9/1991 | Castillo et al. |
| 5,049,134 A | 9/1991 | Golding et al. |
| 5,059,174 A | 10/1991 | Vaillancourt |
| 5,061,256 A | 10/1991 | Wampler |
| 5,074,756 A | 12/1991 | Davis |
| 5,089,016 A | 2/1992 | Millner et al. |
| 5,092,844 A | 3/1992 | Schwartz et al. |
| 5,098,256 A | 3/1992 | Smith |
| 5,106,368 A | 4/1992 | Uldall et al. |
| 5,112,200 A | 5/1992 | Isaacson et al. |
| 5,112,292 A | 5/1992 | Hwang et al. |
| 5,112,349 A | 5/1992 | Summers et al. |
| 5,129,883 A | 7/1992 | Black |
| 5,142,155 A | 8/1992 | Mauze et al. |
| 5,147,186 A | 9/1992 | Buckholtz |
| 5,163,910 A | 11/1992 | Schwartz et al. |
| 5,171,212 A | 12/1992 | Buck et al. |
| 5,190,528 A | 3/1993 | Fonger et al. |
| 5,201,679 A | 4/1993 | Velte et al. |
| 5,211,546 A | 5/1993 | Isaacson et al. |
| 5,221,270 A | 6/1993 | Parker |
| 5,234,416 A | 8/1993 | Macaulay et al. |
| 5,282,787 A | 2/1994 | Wortrich |
| 5,290,227 A | 3/1994 | Pasque |
| 5,300,112 A | 4/1994 | Barr |
| 5,312,341 A | 5/1994 | Turi |
| 5,344,443 A | 9/1994 | Palma et al. |
| 5,346,458 A | 9/1994 | Affeld |
| 5,360,317 A | 11/1994 | Clausen et al. |
| 5,364,342 A | 11/1994 | Beuchat et al. |
| 5,376,114 A | 12/1994 | Jarvik |
| 5,393,197 A | 2/1995 | Lemont et al. |
| 5,393,207 A | 2/1995 | Maher et al. |
| 5,397,222 A | 3/1995 | Moss et al. |
| 5,405,341 A | 4/1995 | Martin |
| 5,405,383 A | 4/1995 | Barr |
| 5,437,541 A | 8/1995 | Vainrub et al. |
| 5,449,342 A | 9/1995 | Hirose et al. |
| 5,458,459 A | 10/1995 | Hubbard et al. |
| 5,490,763 A | 2/1996 | Abrams et al. |
| 5,505,701 A | 4/1996 | Anaya Fernandez de Lomana |
| 5,527,159 A | 6/1996 | Bozeman, Jr. et al. |
| 5,533,957 A | 7/1996 | Aldea |
| 5,534,287 A | 7/1996 | Lukic |
| 5,586,868 A | 12/1996 | Lawless et al. |
| 5,588,812 A | 12/1996 | Taylor et al. |
| 5,601,420 A | 2/1997 | Warner et al. |
| 5,613,935 A | 3/1997 | Jarvik |
| 5,643,226 A | 7/1997 | Cosgrove et al. |
| 5,678,306 A | 10/1997 | Bozeman, Jr. et al. |
| 5,692,882 A | 12/1997 | Bozeman et al. |
| 5,702,418 A | 12/1997 | Ravenscroft |
| 5,704,926 A | 1/1998 | Sutton |
| 5,707,218 A | 1/1998 | Maher et al. |
| 5,722,930 A | 3/1998 | Larson et al. |
| 5,725,513 A | 3/1998 | Ju et al. |
| 5,725,570 A | 3/1998 | Heath |
| 5,730,628 A | 3/1998 | Hawkins |
| 5,735,897 A | 4/1998 | Buirge |
| 5,738,649 A | 4/1998 | Macoviak |
| 5,741,234 A | 4/1998 | Aboul-Hosn |
| 5,741,429 A | 4/1998 | Donadio, III et al. |
| 5,746,709 A | 5/1998 | Rom et al. |
| 5,749,855 A | 5/1998 | Reitan |
| 5,755,784 A | 5/1998 | Jarvik |
| 5,776,111 A | 7/1998 | Tesio |
| 5,776,161 A | 7/1998 | Globerman |
| 5,776,190 A | 7/1998 | Jarvik |
| 5,779,721 A | 7/1998 | Nash |
| 5,807,311 A | 9/1998 | Palestrant |
| 5,814,011 A | 9/1998 | Corace |
| 5,824,070 A | 10/1998 | Jarvik |
| 5,851,174 A | 12/1998 | Jarvik et al. |
| 5,868,702 A | 2/1999 | Stevens |
| 5,868,703 A | 2/1999 | Bertolero |
| 5,888,241 A | 3/1999 | Jarvik |
| 5,888,242 A | 3/1999 | Antaki et al. |
| 5,904,668 A | 5/1999 | Hyman et al. |
| 5,911,685 A | 6/1999 | Siess et al. |
| 5,921,913 A | 7/1999 | Siess |
| 5,927,956 A | 7/1999 | Lim et al. |
| 5,941,813 A | 8/1999 | Sievers et al. |
| 5,951,263 A | 9/1999 | Taylor et al. |
| 5,957,941 A | 9/1999 | Ream |
| 5,964,694 A | 10/1999 | Siess et al. |
| 5,993,420 A | 11/1999 | Hyman et al. |
| 6,007,478 A | 12/1999 | Siess et al. |
| 6,007,479 A | 12/1999 | Rottenberg et al. |
| 6,015,272 A | 1/2000 | Antaki et al. |
| 6,015,434 A | 1/2000 | Yamane |
| 6,018,208 A | 1/2000 | Maher et al. |
| 6,027,863 A | 2/2000 | Donadio, III et al. |
| 6,056,719 A | 5/2000 | Mickley |

(56) References Cited

U.S. PATENT DOCUMENTS

| | | |
|---|---|---|
| 6,058,593 A | 5/2000 | Siess |
| 6,059,760 A | 5/2000 | Sandmore et al. |
| 6,068,610 A | 5/2000 | Ellis et al. |
| 6,071,093 A | 6/2000 | Hart |
| 6,083,260 A | 7/2000 | Aboul-Hosn |
| 6,086,527 A | 7/2000 | Talpade |
| 6,086,570 A | 7/2000 | Aboul-Hosn et al. |
| 6,106,494 A | 8/2000 | Saravia et al. |
| 6,109,895 A | 8/2000 | Ray et al. |
| 6,113,536 A | 9/2000 | Aboul-Hosn et al. |
| 6,123,659 A | 9/2000 | Le Blanc et al. |
| 6,123,725 A | 9/2000 | Aboul-Hosn |
| 6,132,363 A | 10/2000 | Freed et al. |
| 6,135,943 A | 10/2000 | Yu et al. |
| 6,136,025 A | 10/2000 | Barbut et al. |
| 6,139,487 A | 10/2000 | Siess |
| 6,152,704 A | 11/2000 | Aboul-Hosn et al. |
| 6,162,194 A | 12/2000 | Shipp |
| 6,176,822 B1 | 1/2001 | Nix et al. |
| 6,176,848 B1 | 1/2001 | Rau et al. |
| 6,186,665 B1 | 2/2001 | Maher et al. |
| 6,190,304 B1 | 2/2001 | Downey et al. |
| 6,200,260 B1 | 3/2001 | Bolling |
| 6,203,528 B1 | 3/2001 | Deckert et al. |
| 6,210,133 B1 | 4/2001 | Aboul-Hosn et al. |
| 6,210,397 B1 | 4/2001 | Aboul-Hosn et al. |
| 6,214,846 B1 | 4/2001 | Elliott |
| 6,217,541 B1 | 4/2001 | Yu |
| 6,227,797 B1 | 5/2001 | Watterson et al. |
| 6,228,063 B1 | 5/2001 | Aboul-Hosn |
| 6,234,960 B1 | 5/2001 | Aboul-Hosn et al. |
| 6,234,995 B1 | 5/2001 | Peacock, III |
| 6,245,007 B1 | 6/2001 | Bedingham et al. |
| 6,245,026 B1 | 6/2001 | Campbell et al. |
| 6,247,892 B1 | 6/2001 | Kazatchkov et al. |
| 6,248,091 B1 | 6/2001 | Voelker |
| 6,254,359 B1 | 7/2001 | Aber |
| 6,254,564 B1 | 7/2001 | Wilk et al. |
| 6,287,319 B1 | 9/2001 | Aboul-Hosn et al. |
| 6,287,336 B1 | 9/2001 | Globerman et al. |
| 6,295,877 B1 | 10/2001 | Aboul-Hosn et al. |
| 6,299,635 B1 | 10/2001 | Frantzen |
| 6,305,962 B1 | 10/2001 | Maher et al. |
| 6,387,037 B1 | 5/2002 | Bolling et al. |
| 6,395,026 B1 | 5/2002 | Aboul-Hosn et al. |
| 6,413,222 B1 | 7/2002 | Pantages et al. |
| 6,422,990 B1 | 7/2002 | Prem |
| 6,425,007 B1 | 7/2002 | Messinger |
| 6,428,464 B1 | 8/2002 | Bolling |
| 6,447,441 B1 | 9/2002 | Yu et al. |
| 6,468,298 B1 | 10/2002 | Pelton |
| 6,494,694 B2 | 12/2002 | Lawless et al. |
| 6,503,224 B1 | 1/2003 | Forman et al. |
| 6,508,777 B1 | 1/2003 | Macoviak et al. |
| 6,508,787 B2 | 1/2003 | Erbel et al. |
| 6,517,315 B2 | 2/2003 | Belady |
| 6,517,528 B1 | 2/2003 | Pantages et al. |
| 6,532,964 B2 | 3/2003 | Aboul-Hosn et al. |
| 6,533,716 B1 | 3/2003 | Schmitz-Rode et al. |
| 6,544,216 B1 | 4/2003 | Sammler et al. |
| 6,547,519 B2 | 4/2003 | de Blanc et al. |
| 6,565,598 B1 | 5/2003 | Lootz |
| 6,572,349 B2 | 6/2003 | Sorensen et al. |
| 6,609,883 B2 | 8/2003 | Woodard et al. |
| 6,610,004 B2 | 8/2003 | Viole et al. |
| 6,613,008 B2 | 9/2003 | Aboul-Hosn et al. |
| 6,616,323 B2 | 9/2003 | McGill |
| 6,623,420 B2 | 9/2003 | Reich et al. |
| 6,623,475 B1 | 9/2003 | Siess |
| 6,641,558 B1 | 11/2003 | Aboul-Hosn et al. |
| 6,645,241 B1 | 11/2003 | Strecker |
| 6,660,014 B2 | 12/2003 | Demarais et al. |
| 6,673,105 B1 | 1/2004 | Chen |
| 6,692,318 B2 | 2/2004 | McBride |
| 6,709,418 B1 | 3/2004 | Aboul-Hosn et al. |
| 6,716,189 B1 | 4/2004 | Jarvik et al. |
| 6,749,598 B1 | 6/2004 | Keren et al. |
| 6,776,578 B2 | 8/2004 | Belady |
| 6,776,794 B1 | 8/2004 | Hong et al. |
| 6,783,328 B2 | 8/2004 | Lucke et al. |
| 6,790,171 B1 | 9/2004 | Grundeman et al. |
| 6,794,784 B2 | 9/2004 | Takahashi et al. |
| 6,794,789 B2 | 9/2004 | Siess et al. |
| 6,814,713 B2 | 11/2004 | Aboul-Hosn et al. |
| 6,817,836 B2 | 11/2004 | Nose et al. |
| 6,835,049 B2 | 12/2004 | Ray |
| 6,860,713 B2 | 3/2005 | Hoover |
| 6,866,625 B1 | 3/2005 | Avre et al. |
| 6,866,805 B2 | 3/2005 | Hong et al. |
| 6,887,215 B2 | 5/2005 | McWeeney |
| 6,889,082 B2 | 5/2005 | Bolling et al. |
| 6,901,289 B2 | 5/2005 | Dahl et al. |
| 6,926,662 B1 | 8/2005 | Aboul-Hosn et al. |
| 6,935,344 B1 | 8/2005 | Aboul-Hosn et al. |
| 6,942,611 B2 | 9/2005 | Siess |
| 6,949,066 B2 | 9/2005 | Bearnson et al. |
| 6,962,488 B2 | 11/2005 | Davis et al. |
| 6,966,748 B2 | 11/2005 | Woodard et al. |
| 6,972,956 B2 | 12/2005 | Franz et al. |
| 6,974,436 B1 | 12/2005 | Aboul-Hosn et al. |
| 6,981,942 B2 | 1/2006 | Khaw et al. |
| 6,984,392 B2 | 1/2006 | Bechert et al. |
| 7,010,954 B2 | 3/2006 | Siess et al. |
| 7,011,620 B1 | 3/2006 | Siess |
| 7,014,417 B2 | 3/2006 | Salomon |
| 7,018,182 B2 | 3/2006 | O'Mahony et al. |
| 7,022,100 B1 | 4/2006 | Aboul-Hosn et al. |
| 7,027,875 B2 | 4/2006 | Siess et al. |
| 7,037,069 B2 | 5/2006 | Arnold et al. |
| 7,070,555 B2 | 7/2006 | Siess |
| 7,122,019 B1 | 10/2006 | Kesten et al. |
| 7,125,376 B2 | 10/2006 | Viole et al. |
| 7,144,365 B2 | 12/2006 | Bolling et al. |
| 7,150,711 B2 | 12/2006 | Nusser et al. |
| 7,160,243 B2 | 1/2007 | Medvedev |
| 7,172,551 B2 | 2/2007 | Leasure |
| 7,175,588 B2 | 2/2007 | Morello |
| 7,214,038 B2 | 5/2007 | Saxer et al. |
| 7,229,258 B2 | 6/2007 | Wood et al. |
| 7,238,010 B2 | 7/2007 | Hershberger et al. |
| 7,241,257 B1 | 7/2007 | Ainsworth et al. |
| 7,262,531 B2 | 8/2007 | Li et al. |
| 7,264,606 B2 | 9/2007 | Jarvik et al. |
| 7,267,667 B2 | 9/2007 | Houde et al. |
| 7,284,956 B2 | 10/2007 | Nose et al. |
| 7,288,111 B1 | 10/2007 | Holloway et al. |
| 7,329,236 B2 | 2/2008 | Keren et al. |
| 7,331,921 B2 | 2/2008 | Viole et al. |
| 7,335,192 B2 | 2/2008 | Keren et al. |
| 7,341,570 B2 | 3/2008 | Keren et al. |
| 7,381,179 B2 | 6/2008 | Aboul-Hosn et al. |
| 7,393,181 B2 | 7/2008 | McBride et al. |
| 7,393,189 B2 | 7/2008 | Davis et al. |
| 7,469,716 B2 | 12/2008 | Parrino et al. |
| 7,478,999 B2 | 1/2009 | Limoges |
| 7,491,163 B2 | 2/2009 | Viole et al. |
| 7,534,258 B2 | 5/2009 | Gomez |
| 7,547,200 B2 | 6/2009 | O'Mahony et al. |
| 7,605,298 B2 | 10/2009 | Bechert et al. |
| 7,619,560 B2 | 11/2009 | Penna |
| 7,632,079 B2 | 12/2009 | Hershberger et al. |
| 7,645,225 B2 | 1/2010 | Medvedev et al. |
| 7,657,324 B2 | 2/2010 | Westlund et al. |
| 7,682,673 B2 | 3/2010 | Houston et al. |
| 7,731,675 B2 | 6/2010 | Aboul-Hosn et al. |
| 7,736,296 B2 | 6/2010 | Siess et al. |
| 7,744,566 B2 | 6/2010 | Pirovano et al. |
| 7,758,521 B2 | 7/2010 | Morris et al. |
| 7,766,892 B2 | 8/2010 | Keren et al. |
| 7,780,628 B1 | 8/2010 | Keren et al. |
| 7,785,246 B2 | 8/2010 | Aboul-Hosn et al. |
| 7,811,279 B2 | 10/2010 | John |
| 7,819,833 B2 | 10/2010 | Ainsworth et al. |
| 7,820,205 B2 | 10/2010 | Takakusagi et al. |

(56) References Cited

U.S. PATENT DOCUMENTS

| | | |
|---|---|---|
| 7,828,710 B2 | 11/2010 | Shifflette |
| 7,841,976 B2 | 11/2010 | McBride et al. |
| 7,878,967 B1 | 2/2011 | Khanal |
| 7,927,068 B2 | 4/2011 | McBride et al. |
| 7,934,912 B2 | 5/2011 | Voltenburg, Jr. et al. |
| 7,935,102 B2 | 5/2011 | Breznock et al. |
| 7,942,804 B2 | 5/2011 | Khaw |
| 7,942,844 B2 | 5/2011 | Moberg et al. |
| 7,955,365 B2 | 6/2011 | Doty |
| 7,993,259 B2 | 8/2011 | Kang et al. |
| 7,998,054 B2 | 8/2011 | Bolling |
| 8,012,079 B2 | 9/2011 | Delgado |
| 8,025,647 B2 | 9/2011 | Siess et al. |
| 8,052,399 B2 | 11/2011 | Stemple et al. |
| 8,062,008 B2 | 11/2011 | Voltenburg, Jr. et al. |
| 8,079,948 B2 | 12/2011 | Shifflette |
| 8,083,503 B2 | 12/2011 | Voltenburg et al. |
| 8,110,267 B2 | 2/2012 | Houston et al. |
| 8,114,008 B2 | 2/2012 | Hidaka et al. |
| 8,123,669 B2 | 2/2012 | Siess et al. |
| 8,142,400 B2 | 3/2012 | Rotem et al. |
| 8,177,703 B2 | 5/2012 | Smith et al. |
| 8,206,350 B2 | 6/2012 | Mann et al. |
| 8,209,015 B2 | 6/2012 | Glenn |
| 8,235,943 B2 | 8/2012 | Breznock et al. |
| 8,236,044 B2 | 8/2012 | Robaina |
| 8,255,050 B2 | 8/2012 | Mohl |
| 8,257,054 B2 | 9/2012 | Voltenburg et al. |
| 8,257,312 B2 | 9/2012 | Duffy |
| 8,262,619 B2 | 9/2012 | Chebator et al. |
| 8,277,470 B2 | 10/2012 | Demarais et al. |
| 8,317,715 B2 | 11/2012 | Belleville et al. |
| 8,329,913 B2 | 12/2012 | Murata et al. |
| 8,348,991 B2 | 1/2013 | Weber et al. |
| 8,364,278 B2 | 1/2013 | Pianca et al. |
| 8,371,832 B2 | 2/2013 | Rotem et al. |
| 8,376,707 B2 | 2/2013 | McBride et al. |
| 8,382,818 B2 | 2/2013 | Davis et al. |
| 8,388,565 B2 | 3/2013 | Shifflette |
| 8,388,582 B2 | 3/2013 | Eubanks et al. |
| 8,409,128 B2 | 4/2013 | Ferrari |
| 8,439,859 B2 | 5/2013 | Pfeffer et al. |
| 8,449,443 B2 | 5/2013 | Rodefeld |
| 8,485,961 B2 | 7/2013 | Campbell et al. |
| 8,489,190 B2 | 7/2013 | Pfeffer et al. |
| 8,491,285 B2 | 7/2013 | Haser et al. |
| 8,535,211 B2 | 9/2013 | Campbell et al. |
| 8,540,615 B2 | 9/2013 | Aboul-Hosn et al. |
| 8,545,379 B2 | 10/2013 | Marseille et al. |
| 8,545,380 B2 | 10/2013 | Farnan et al. |
| 8,579,858 B2 | 11/2013 | Reitan |
| 8,585,572 B2 | 11/2013 | Mehmanesh |
| 8,591,393 B2 | 11/2013 | Walters et al. |
| 8,597,170 B2 | 12/2013 | Walters et al. |
| 8,617,239 B2 | 12/2013 | Reitan |
| 8,684,904 B2 | 4/2014 | Campbell et al. |
| 8,721,516 B2 | 5/2014 | Scheckel |
| 8,721,517 B2 | 5/2014 | Zeng et al. |
| 8,727,959 B2 | 5/2014 | Reitan et al. |
| 8,734,331 B2 | 5/2014 | Evans et al. |
| 8,795,576 B2 | 8/2014 | Tao et al. |
| 8,801,590 B2 | 8/2014 | Mohl |
| 8,814,776 B2 | 8/2014 | Hastie et al. |
| 8,814,933 B2 | 8/2014 | Siess |
| 8,849,398 B2 | 9/2014 | Evans |
| 8,944,748 B2 | 2/2015 | Liebing |
| 8,992,406 B2 | 3/2015 | Corbett |
| 8,998,792 B2 | 4/2015 | Scheckel |
| 9,028,216 B2 | 5/2015 | Schumacher et al. |
| 2002/0094287 A1 | 7/2002 | Davis |
| 2003/0018380 A1 | 1/2003 | Craig et al. |
| 2003/0205233 A1 | 11/2003 | Aboul-Hosn et al. |
| 2003/0208097 A1 | 11/2003 | Aboul-Hosn et al. |
| 2003/0225366 A1 | 12/2003 | Morgan et al. |
| 2003/0231959 A1 | 12/2003 | Snider |
| 2004/0116862 A1 | 6/2004 | Ray |
| 2004/0253129 A1 | 12/2004 | Sorensen et al. |
| 2005/0013698 A1 | 1/2005 | Davis |
| 2005/0049696 A1 | 3/2005 | Siess et al. |
| 2005/0085683 A1 | 4/2005 | Bolling et al. |
| 2005/0113631 A1 | 5/2005 | Bolling et al. |
| 2005/0165269 A9 | 7/2005 | Aboul-Hosn et al. |
| 2005/0277912 A1* | 12/2005 | John .......... A61M 25/0026 604/890.1 |
| 2006/0018943 A1 | 1/2006 | Bechert et al. |
| 2006/0058869 A1 | 3/2006 | Olson et al. |
| 2006/0063965 A1 | 3/2006 | Aboul-Hosn et al. |
| 2006/0089521 A1 | 4/2006 | Chang |
| 2006/0155158 A1 | 7/2006 | Aboul-Hosn |
| 2006/0167404 A1 | 7/2006 | Pirovano et al. |
| 2006/0264695 A1 | 11/2006 | Viole et al. |
| 2006/0270894 A1 | 11/2006 | Viole et al. |
| 2007/0100314 A1 | 5/2007 | Keren et al. |
| 2007/0212240 A1 | 9/2007 | Voyeux et al. |
| 2007/0217932 A1 | 9/2007 | Voyeux et al. |
| 2007/0248477 A1 | 10/2007 | Nazarifar et al. |
| 2008/0015506 A1 | 1/2008 | Davis |
| 2008/0103442 A1 | 5/2008 | Kesten et al. |
| 2008/0119943 A1 | 5/2008 | Armstrong et al. |
| 2008/0132748 A1 | 6/2008 | Shifflete |
| 2008/0167679 A1 | 7/2008 | Papp |
| 2008/0200878 A1 | 8/2008 | Davis et al. |
| 2008/0275290 A1 | 11/2008 | Viole et al. |
| 2009/0053085 A1 | 2/2009 | Thompson et al. |
| 2009/0112312 A1 | 4/2009 | LaRose et al. |
| 2009/0118567 A1 | 5/2009 | Siess |
| 2009/0182188 A1 | 7/2009 | Marseille et al. |
| 2010/0030186 A1 | 2/2010 | Stivland |
| 2010/0041939 A1 | 2/2010 | Siess |
| 2010/0094089 A1 | 4/2010 | Litscher et al. |
| 2010/0127871 A1 | 5/2010 | Pontin |
| 2010/0137802 A1 | 6/2010 | Yodfat et al. |
| 2010/0174239 A1 | 7/2010 | Yodfat et al. |
| 2010/0210895 A1 | 8/2010 | Aboul-Hosn et al. |
| 2010/0268017 A1 | 10/2010 | Siess |
| 2010/0274330 A1 | 10/2010 | Burwell et al. |
| 2011/0015610 A1 | 1/2011 | Plahey et al. |
| 2011/0071338 A1 | 3/2011 | McBride et al. |
| 2011/0076439 A1 | 3/2011 | Zeilon |
| 2011/0218516 A1 | 9/2011 | Grigorov |
| 2011/0237863 A1 | 9/2011 | Ricci et al. |
| 2011/0300010 A1 | 12/2011 | Jarnagin et al. |
| 2012/0004495 A1 | 1/2012 | Bolling |
| 2012/0142994 A1 | 6/2012 | Toellner |
| 2012/0178986 A1 | 7/2012 | Campbell et al. |
| 2012/0220854 A1 | 8/2012 | Messerly et al. |
| 2012/0224970 A1 | 9/2012 | Schumacher et al. |
| 2012/0226097 A1 | 9/2012 | Smith et al. |
| 2012/0245404 A1 | 9/2012 | Smith et al. |
| 2012/0265002 A1 | 10/2012 | Roehn et al. |
| 2013/0041202 A1 | 2/2013 | Toellner |
| 2013/0053622 A1 | 2/2013 | Corbett |
| 2013/0053623 A1 | 2/2013 | Evans et al. |
| 2013/0053693 A1 | 2/2013 | Breznock et al. |
| 2013/0066140 A1 | 3/2013 | McBride et al. |
| 2013/0085318 A1 | 4/2013 | Toellner |
| 2013/0129503 A1 | 5/2013 | McBride et al. |
| 2013/0138205 A1 | 5/2013 | Kushwaha et al. |
| 2013/0237744 A1 | 9/2013 | Pfeffer et al. |
| 2013/0303969 A1 | 11/2013 | Keenan et al. |
| 2013/0303970 A1 | 11/2013 | Keenan et al. |
| 2013/0345492 A1 | 12/2013 | Pfeffer et al. |
| 2014/0005467 A1 | 1/2014 | Farnan et al. |
| 2014/0010686 A1 | 1/2014 | Tanner et al. |
| 2014/0012065 A1 | 1/2014 | Fitzgerald et al. |
| 2014/0275726 A1 | 9/2014 | Zeng et al. |
| 2015/0051435 A1 | 2/2015 | Siess et al. |
| 2015/0080743 A1 | 3/2015 | Siess |

(56) References Cited

U.S. PATENT DOCUMENTS

| | | |
|---|---|---|
| 2015/0087890 A1 | 3/2015 | Spanier et al. |
| 2015/0151032 A1 | 6/2015 | Voskoboynikov |

FOREIGN PATENT DOCUMENTS

| | | |
|---|---|---|
| EP | 0 533 432 | 9/1992 |
| EP | 1 207 934 | 5/2002 |
| EP | 1 591 079 A1 | 11/2005 |
| EP | 2 298 374 A1 | 3/2011 |
| EP | 2 263 732 | 12/2012 |
| FR | 2267800 | 4/1974 |
| GB | 2 239 675 A | 7/1991 |
| JP | S48-23295 | 3/1973 |
| JP | 06-114101 | 4/1994 |
| JP | 10-099447 | 4/1998 |
| JP | 2011-000620 | 9/2005 |
| TW | 500877 | 9/2002 |
| WO | WO 89/05164 | 6/1989 |
| WO | WO 97/15228 | 5/1997 |
| WO | WO 97/37697 | 10/1997 |
| WO | WO 00/12148 | 3/2000 |
| WO | WO 00/19097 | 4/2000 |
| WO | WO 00/69489 | 11/2000 |
| WO | WO 01/24867 | 4/2001 |
| WO | WO 02/070039 | 9/2002 |
| WO | WO 03/103745 | 12/2003 |
| WO | WO 2005/089674 | 9/2005 |
| WO | WO 2005/123158 | 12/2005 |
| WO | WO 2009/073037 | 6/2009 |
| WO | WO 2009/076460 A2 | 6/2009 |
| WO | WO 2010/127871 | 11/2010 |
| WO | WO 2010/133567 | 11/2010 |
| WO | WO 2010/149393 | 12/2010 |
| WO | WO 2011/035926 | 3/2011 |
| WO | WO 2011/035929 | 3/2011 |
| WO | WO 2011/039091 A1 | 4/2011 |
| WO | WO 2011/076439 | 6/2011 |
| WO | WO 2011/089022 | 7/2011 |
| WO | WO 2012/007140 | 1/2012 |
| WO | WO 2012/007141 | 1/2012 |
| WO | WO 2013/160407 A1 | 10/2013 |
| WO | WO 2014/019274 A1 | 2/2014 |

OTHER PUBLICATIONS

ABIOMED—Recovering Hearts. Saving Lives., Impella 2.5 System, Instructions for Use, Jul. 2007, in 86 sheets.
Barras et al., "Nitinol—Its Use in Vascular Surgery and Other Applications," Eur. J. Vasc. Endovasc. Surg., 2000, pp. 564-569; vol. 19.
Biscarini et al., "Enhanced Nitinol Properties for Biomedical Applications," Recent Patents on Biomedical Engineering, 2008, pp. 180-196, vol. 1(3).
Cardiovascular Diseases (CVDs) Fact Sheet No. 317; World Health Organization [Online], Sep. 2011. http://www.who.int/mediacentre/factsheets/fs317/en/index.html, accessed on Aug. 29, 2012.
Duerig et a., "An Overview of Nitinol Medical Applications," Materials Science Engineering, 1999, pp. 149-160; vol. A273.
European Search Report received in European Patent Application No. 05799883.3, dated May 10, 2011, in 4 pages.
Extended European Search Report received in European Patent Application No. 07753903.9, dated Oct. 8, 2012, in 7 pages.
Federal and Drug Administration 510(k) Summary for Predicate Device IMPELLA 2.5 (K112892), prepared Sep. 5, 2012.
Grech, "Percutaneous Coronary Intervention. I: History and Development," BMJ., May 17, 2003, pp. 1080-1082, vol. 326.
Hsu et al., "Review of Recent Patents on Foldable Ventricular Assist Devices," Recent Patents on Biomedical Engineering, 2012, pp. 208-222, vol. 5.
Ide et al., "Evaluation of the Pulsatility of a New Pulsatile Left Ventricular Assist Device—the Integrated Cardioassist Catheter-in Dogs," J. of Thorac and Cardiovasc Sur, Feb. 1994, pp. 569-0575, vol. 107(2).
Ide et al., "Hemodynamic Evaluation of a New Left Ventricular Assist Device: An Integrated Cardioassist Catheter as a Pulsatile Left Ventricle—Femoral Artery Bypass," Blackwell Scientific Publications, Inc., 1992, pp. 286-290, vol. 16(3).
International Preliminary Examination Report received in International Patent Application No. PCT/US2003/04853, mailed on Jul. 26, 2004, in 5 pages.
International Preliminary Examination Report received in International Patent Application No. PCT/US2003/04401, dated May 18, 2004, in 4 pages.
International Preliminary Report on Patentability and Written Opinion of the International Searching Authority received in International Patent Application No. PCT/US2005/033416, mailed on Mar. 20, 2007, in 7 pages.
International Preliminary Report on Patentability and Written Opinion of the International Searching Authority received in International Patent Application No. PCT/US2007/007313, mailed on Sep. 23, 2008, in 6 pages.
International Search Report and Written Opinion received in International Patent Application No. PCT/US2005/033416, mailed on Dec. 11, 2006, in 8 pages.
International Search Report and Written Opinion received in International Patent Application No. PCT/US2007/007313, mailed on Mar. 4, 2008, in 6 pages.
International Search Report and Written Opinion received in International Patent Application No. PCT/US2012/020382, mailed on Jul. 31, 2012, in 11 pages.
International Search Report and Written Opinion received in International Patent Application No. PCT/US2012/020369, mailed on Jul. 30, 2012, in 10 pages.
International Search Report and Written Opinion received in International Patent Application No. PCT/US2012/020553, mailed on Aug. 17, 2012, in 8 pages.
International Search Report and Written Opinion received in International Patent Application No. PCT/US2012/020383, mailed on Aug. 17, 2012; in 9 pages.
International Search Report and Written Opinion received in International Patent Application No. PCT/US2013/040798, mailed Aug. 21, 2013, in 16 pages.
International Search Report and Written Opinion received in International Patent Application No. PCT/US2013/040799, mailed Aug. 21, 2013, in 19 pages.
International Search Report and Written Opinion received in International Patent Application No. PCT/US2013/040809, mailed Sep. 2, 2013, in 25 pages.
International Search Report and Written Opinion received in International Patent Application No. PCT/US2013/048332, mailed Oct. 16, 2013, in 17 pages.
International Search Report and Written Opinion received in International Patent Application No. PCT/US2013/048343, mailed Oct. 11, 2013, in 15 pages.
International Search Report and Written Opinion received in International Patent Application No. PCT/US2014/020878, mailed May 7, 2014, in 13 pages.
International Search Report received in International Patent Application No. PCT/US2003/004401, mailed on Nov. 10, 2003, in 9 pages.
International Search Report received in International Patent Application No. PCT/US2003/004853, mailed on Jul. 3, 2003, in 3 pages.
International Search Report Written Opinion received in International Patent Application No. PCT/US2010/040847, mailed on Dec. 14, 2010, in 17 pages.
Krishnamani et al., "Emerging Ventricular Assist Devices for Long-Term Cardiac Support," National Review, Cardiology, Feb. 2010, pp. 71-76, vol. 7.
Mihaylov et al., "Development of a New Introduction Technique for the Pulsatile Catheter Pump," Artificial Organs, 1997, pp. 425-427; vol. 21(5).
Mihaylov et al., "Evaluation of the Optimal Driving Mode During Left Ventricular Assist with Pulsatile Catheter Pump in Calves," Artificial Organs, 1999, pp. 1117-1122; vol. 23(12).

(56) References Cited

OTHER PUBLICATIONS

Morgan, "Medical Shape Memory Alloy Applications—The Market and its Products," Materials Science and Engineering, 2004, pp. 16-23, vol. A 378.
Morsink et al., "Numerical Modelling of Blood Flow Behaviour in the Valved Catheter of the PUCA-Pump, a LVAD," The International Journal of Artificial Organs, 1997, pp. 277-284; vol. 20(5).
Nishimura et al, "The Enabler Cannula Pump: A Novel Circulatory Support System," The International Journal of Artificial Organs, 1999, pp. 317-323; vol. 22(5).
Petrini et al., "Biomedical Applications of Shape Memory Alloys," Journal of Metallurgy, 2011, pp. 1-15.
Raess et al., "Impella 2.5," J. Cardiovasc. Transl. Res., 2009, pp. 168-172, vol. 2(2).
Rakhorst et al., "In Vitro Evaluation of the Influence of Pulsatile Intraventricular Pumping on Ventricular Pressure Patterns," Artificial Organs, 1994, pp. 494-499, vol. 18(7).
Reitan et al., "Hemodynamic Effects of a New Percutaneous Circulatory Support Device in a Left Ventricular Failure Model," ASAIO Journal, 2003, pp. 731-736, vol. 49.
Reitan et al., "Hydrodynamic Properties of a New Percutaneous Intra-Aortic Axial Flow Pump," ASAIO Journal 2000, pp. 323-328.
Schmitz-Rode et al., "An Expandable Percutaneous Catheter Pump for Left Ventricular Support," Journal of the American College of Cardiology, 2005, pp. 1856-1861, vol. 45(11).
Shabari et al., "Improved Hemodynamics with a Novel Miniaturized Intra-Aortic Axial Flow Pump in a Porcine Model of Acute Left Ventricular Dysfunction," ASAIO Journal, 2013, pp. 240-245; vol. 59.
Sharony et al, "Cardiopulmonary Support and Physiology—The Intra-Aortic Cannula Pump: A Novel Assist Device for the Acutely Failing Heart," The Journal of Thoracic and Cardiovascular Surgery, Nov. 1992, pp. 924-929, vol. 118(5).
Sharony et al., "Right Heart Support During Off-Pump Coronary Artery Surgery—A Multi-Center Study," The Heart Surgery Forum, 2002, pp. 13-16, vol. 5(1).
Smith et al., "First-In-Man Study of the Reitan Catheter Pump for Circulatory Support in Patients Undergoing High-Risk Percutaneous Coronary Intervention," Catheterization and Cardiovascular Interventions, 2009, pp. 859-865, vol. 73(7).
Sokolowski et al., "Medical Applications of Shape Memory Polymers," Biomed. Mater. 2007, pp. S23-S27, vol. 2.
"Statistical Analysis and Clinical Experience with the Recover® Pump Systems", Impella CardioSystems GmbH, 2 sheets.
Stoeckel et al., "Self-Expanding Nitinol Stents—Material and Design Considerations," European Radiology, 2003, in 13 sheets.
Stolinski et al., "The heart-pump interaction: effects of a microaxial blood pump," International Journal of Artificial Organs, 2002, pp. 1082-1088, vol. 25, Issue 11.
Supplemental European Search Report received from the European Patent Office in EP Application No. EP 05799883 dated Mar. 19, 2010, 3 pages.
Takagaki et al., "A Novel Miniature Ventricular Assist Device for Hemodynamic Support," ASAIO Journal, 2001, pp. 412-416; vol. 47.
Throckmorton et al., "Flexible Impeller Blades in an Axial Flow Pump for Intravascular Cavopulmonary Assistance of the Fontan Physiology," Cardiovascular Engineering and Technology, Dec. 2010, pp. 244-255, vol. 1(4).
Verkerke et al., "Numerical Simulation of the PUCA Pump, A Left Ventricular Assist Device," Abstracts of the XIXth ESAO Congress, The International Journal of Artificial Organs, 1992, p. 543, vol. 15(9).
Verkerke et al., "Numerical Simulation of the Pulsating Catheter Pump: A Left Ventricular Assist Device," Artificial Organs, 1999, pp. 924-931, vol. 23(10).
Verkerke et al., "The PUCA Pump: A Left Ventricular Assist Device," Artificial Organs, 1993, pp. 365-368, vol. 17(5).
Wampler et al., "The Sternotomy Hemopump, A Second Generation Intraarterial Ventricular Assist Device," ASAIO Journal, 1993, pp. M218-M223, vol. 39.
Weber et al., "Principles of Impella Cardiac Support," Supplemental to Cardiac Interventions Today, Aug./Sep. 2009.
Written Opinion received in International Patent Application No. PCT/US2003/04853, dated Feb. 25, 2004, 5 pages.
Kunst et al., "Integrated unit for programmable control of the 21F Hemopump and registration of physiological signals," Medical & Biological Engineering & Computing, Nov. 1994, pp. 694-696.
Throckmorton et al., "Uniquely shaped cardiovascular stents enhance the pressure generation of intravascular blood pumps," The Journal of Thoracic and Cardiovascular Surgery, Sep. 2012, pp. 704-709, vol. 133, No. 3.
International Search Report and Written Opinion received in International Patent Application No. PCT/US2014/020790, mailed Aug. 6, 2014, in 11 pages.
Aboul-Hosn et al., "The Hemopump: Clinical Results and Future Applications", Assisted Circulation 4, 1995, in 14 pages.
Compendium of Technical and Scientific Information for the HEMOPUMP Temporary Cardiac Assist System, Johnson & Johnson Interventional Systems, 1988, in 15 pages.
Dekker et al., "Efficacy of a New Intraaortic Propeller Pump vs the Intraaortic Balloon Pump, An Animal Study", Chest, Jun. 2003, vol. 123, No. 6, pp. 2089-2095.
Impella CP®—Instructions for Use & Clinical Reference Manual (United States only), Abiomed, Inc., Jul. 2014, 148 pages, www.abiomed.com.
Impella LD® with the Impella® Controller—Circulatory Support System—Instructions for Use & Clinical Reference Manual (United States only), Abiomed, Inc., Sep. 2010, 132 pages, www.abiomed.com.
International Preliminary Report on Patentability and Written Opinion received in International Patent Application No. PCT/US2014/020878, mailed Sep. 15, 2015, in 8 pages.
International Search Reort and Written Opinion received in International Patent Application No. PCT/US2015/026013, mailed Jul. 8, 2015, in 12 pages.
International Search Report and Written Opinion received in International Patent Application No. PCT/US2015/026014, mailed Jul. 15, 2015, in 13 pages.
International Search Report and Written Opinion received in International Patent Application No. PCT/US2015/026025, mailed Jul. 20, 2015, in 12 pages.
International Search Report and Written Opinion received in International Patent Application No. PCT/US2015/025959, mailed Aug. 28, 2015, in 16 pages.
International Search Report and Written Opinion received in International Patent Application No. PCT/US2015/025960, mailed Sep. 3, 2015, in 15 pages.
International Search Report and Written Opinion received in International Patent Application No. PCT/US2015/045370, mailed Nov. 18, 2015, in 12 pages.
JOMED Reitan Catheter Pump RCP, Percutaneous Circulatory Support, in 10 pages.
JOMED Reitan Catheter Pump RCP, Feb. 18, 2003, in 4 pages.
Minimally Invasive Cardiac Assist JOMED Catheter PumpTM, in 6 pages.
Reitan, Evaluation of a New Percutaneous Cardiac Assist Device, Department of Cardiology, Faculty of Medicine, Lund University, Sweden, 2002, in 172 pages.
Rothman, "The Reitan Catheter Pump: A New Versatile Approach for Hemodynamic Support", London Chest Hospital Barts & The London NHS Trust, Oct. 22-27, 2006 (TCT 2006: Transcatheter Cardiovascular Therapeutics 18th Annual Scientific Symposium, Final Program), in 48 pages.
Sieβ et al., "Hydraulic refinement of an intraarterial microaxial blood pump", The International Journal of Artificial Organs, 1995, vol. 18, No. 5, pp. 273-285.
Sieβ, "Systemanalyse und Entwicklung intravasaler Rotationspumpen zur Herzunterstützung", Helmholtz-Institut fur Blomedixinische Technik an der RWTH Aachen, Jun. 24, 1998, in 105 pages.

(56) References Cited

OTHER PUBLICATIONS

Siess et al., "Basic design criteria for rotary blood pumps," H. Masuda, Rotary Blood Pumps, Springer, Japan, 2000, pp. 69-83.

Siess et al., "Concept, realization, and first in vitro testing of an intraarterial microaxial blood pump," Artificial Organs, 1995, pp. 644-652, vol. 19, No. 7, Blackwell Science, Inc., Boston, International Society for Artificial Organs.

Siess et al., "From a lab type to a product: A retrospective view on Impella's assist technology," Artificial Organs, 2001, pp. 414-421, vol. 25, No. 5, Blackwell Science, Inc., International Society for Artificial Organs.

Siess et al., "System analysis and development of intravascular rotation pumps for cardiac assist," Dissertation, Shaker Verlag, Aachen, 1999, 39 pages.

* cited by examiner

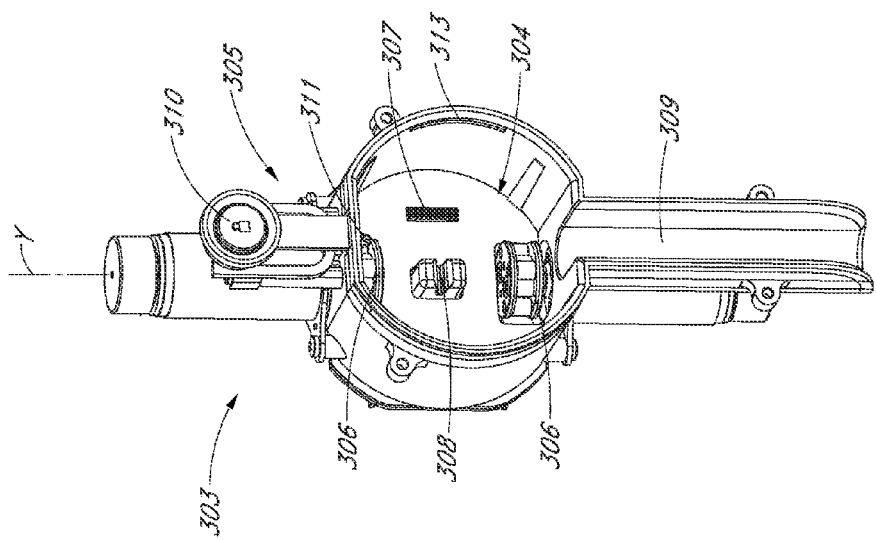
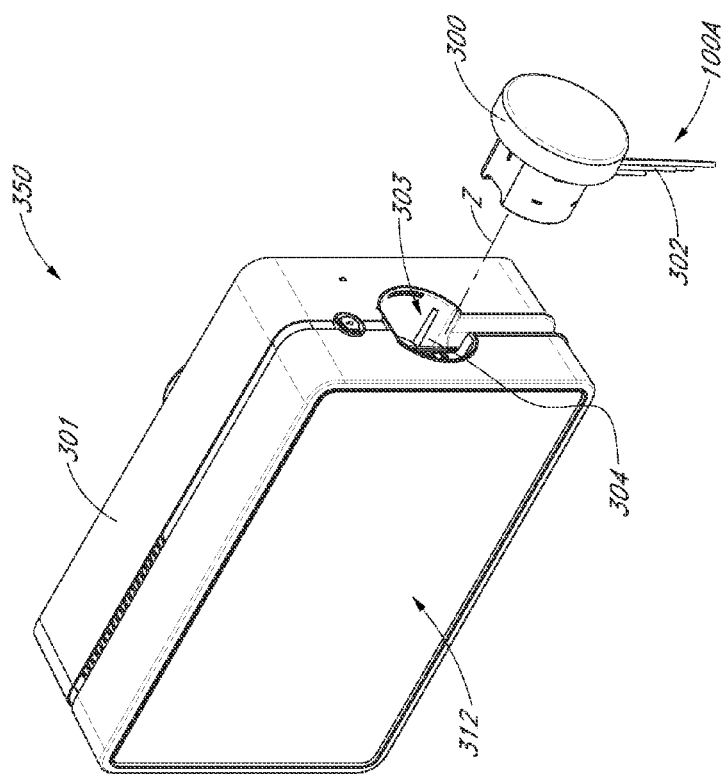
FIG. 3B
FIG. 3A

FLUID HANDLING SYSTEM

INCORPORATION BY REFERENCE TO ANY PRIORITY APPLICATIONS

Any and all applications for which a foreign or domestic priority claim is identified, including U.S. Application No. 61/780,656, filed Mar. 13, 2013, entitled Fluid Handling System, (hereinafter "the '656 priority application") are hereby incorporated by reference.

BACKGROUND OF THE INVENTION

1. Field of the Invention

This application is directed to pumps for mechanical circulatory support of a heart. In particular, this application is directed to a console and controller for a catheter pump and a fluid handling system configured to convey and remove fluids to and from the catheter pump.

2. Description of the Related Art

Heart disease is a major health problem that has high mortality rate. Physicians increasingly use mechanical circulatory support systems for treating heart failure. The treatment of acute heart failure requires a device that can provide support to the patient quickly. Physicians desire treatment options that can be deployed quickly and minimally-invasively.

Intra-aortic balloon pumps (IABP) are currently the most common type of circulatory support devices for treating acute heart failure. IABPs are commonly used to treat heart failure, such as to stabilize a patient after cardiogenic shock, during treatment of acute myocardial infarction (MI) or decompensated heart failure, or to support a patient during high risk percutaneous coronary intervention (PCI). Circulatory support systems may be used alone or with pharmacological treatment.

In a conventional approach, an IABP is positioned in the aorta and actuated in a counterpulsation fashion to provide partial support to the circulatory system. More recently, minimally-invasive rotary blood pumps have been developed in an attempt to increase the level of potential support (i.e., higher flow). A rotary blood pump is typically inserted into the body and connected to the cardiovascular system, for example, to the left ventricle and the ascending aorta to assist the pumping function of the heart. Other known applications pumping venous blood from the right ventricle to the pulmonary artery for support of the right side of the heart. An aim of acute circulatory support devices is to reduce the load on the heart muscle for a period of time, to stabilize the patient prior to heart transplant or for continuing support.

There is a need for improved mechanical circulatory support devices for treating acute heart failure. Fixed cross-section ventricular assist devices designed to provide near full heart flow rate are either too large to be advanced percutaneously (e.g., through the femoral artery without a cutdown) or provide insufficient flow.

There is a need for a pump with improved performance and clinical outcomes. There is a need for a pump that can provide elevated flow rates with reduced risk of hemolysis and thrombosis. There is a need for a pump that can be inserted minimally-invasively and provide sufficient flow rates for various indications while reducing the risk of major adverse events. In one aspect, there is a need for a heart pump that can be placed minimally-invasively, for example, through a 15 FR or 12 FR incision. In one aspect, there is a need for a heart pump that can provide an average flow rate of 4 Lpm or more during operation, for example, at 62 mmHg of head pressure. While the flow rate of a rotary pump can be increased by rotating the impeller faster, higher rotational speeds are known to increase the risk of hemolysis, which can lead to adverse outcomes and in some cases death. Accordingly, in one aspect, there is a need for a pump that can provide sufficient flow at significantly reduced rotational speeds. These and other problems are overcome by the inventions described herein.

Furthermore, in various catheter pump systems, it can be important to provide fluids to an operative device of a catheter assembly (e.g., for lubrication of moving parts and/or treatment fluids to be delivered to the patient), and to remove waste fluids from the patient's body. A controller may be provided to control the flow into and out of the catheter assembly. It can be advantageous to provide improved mechanisms for engaging the catheter assembly with the controller, which may be housed in a console.

Additionally, there is a need to reduce the time to implantation and treatment. In the case of therapy for acute heart failure in particular, the time it takes to start therapy can be critical to survival and good outcomes. For example, a difference of several minutes can be the difference between recovery and permanent brain damage for patients suffering myocardial infarction or cardiogenic shock. Accordingly, a continuing need exists to provide pump systems that can be set up, primed, and inserted faster, easier, and more effectively.

These and other problems are overcome by the inventions described herein.

SUMMARY

There is an urgent need for a pumping device that can be inserted percutaneously and also provide full cardiac rate flows of the left, right, or both the left and right sides of the heart when called for.

In one embodiment, a fluid handling system is disclosed. The system can include a housing. The housing can include one or more pumps, and a controller configured to operate the pump(s). The system can further include a catheter assembly. The catheter assembly may include a catheter body having a proximal portion and an operative device at a distal portion. An infusion system can be in fluid communication with the proximal portion of the catheter body. The infusion system can include a closure member configured to be separate from the housing in a first state and to at least partially secure the infusion system to the housing in a second state. Upon engagement of the closure member with the housing in the second state, the infusion system may be operably engaged with the pump(s).

In another embodiment, a removable interface member for a fluid handling system is disclosed. The interface member can include an interface body sized and shaped to be inserted into an interface aperture of a console housing. An electrical component can be disposed on the interface body. Furthermore, an occlusion bed can be disposed on the interface body. A tube segment can be disposed on the interface body near the occlusion bed. The interface body can be dimensioned such that when the interface body is inserted into the interface aperture of the console housing, a pump in the console housing is operably engaged with the tube segment and the occlusion bed, and an electrical interconnect in the console housing is electrically coupled with the electrical component on the interface body.

In yet another embodiment, a method for operably coupling an infusion system to a console housing is disclosed. The method can comprise positioning an interface body of the infusion system in an interface aperture of the console housing. The interface body can comprise an occlusion bed, a tube segment mounted on the interface body near the occlusion bed, and an electrical component. The method can further comprise inserting the interface body through the interface aperture until a pump roller of the console housing compresses the tube segment against the occlusion bed and until an electrical interconnect of the console housing is electrically coupled to the electrical component of the interface body.

In another embodiment, a method for priming a catheter assembly is disclosed. The catheter assembly can include an elongate body and an operative device. The method can comprise inserting the operative device of the catheter assembly into a priming vessel. The method can further comprise securing a proximal portion of the priming vessel to a distal portion of the elongate body, such that the elongate body is in fluid communication with the priming vessel. Fluid can be delivered through the elongate body and the priming vessel to expel air within the catheter assembly.

BRIEF DESCRIPTION OF THE DRAWINGS

A more complete appreciation of the subject matter of this application and the various advantages thereof can be realized by reference to the following detailed description, in which reference is made to the accompanying drawings in which:

FIG. 3A is a three-dimensional perspective view of a fluid handling system that includes a console and catheter assembly.

FIG. 3B is a three-dimensional perspective view of an interface region of the console shown in FIG. 3A.

Figure 1:
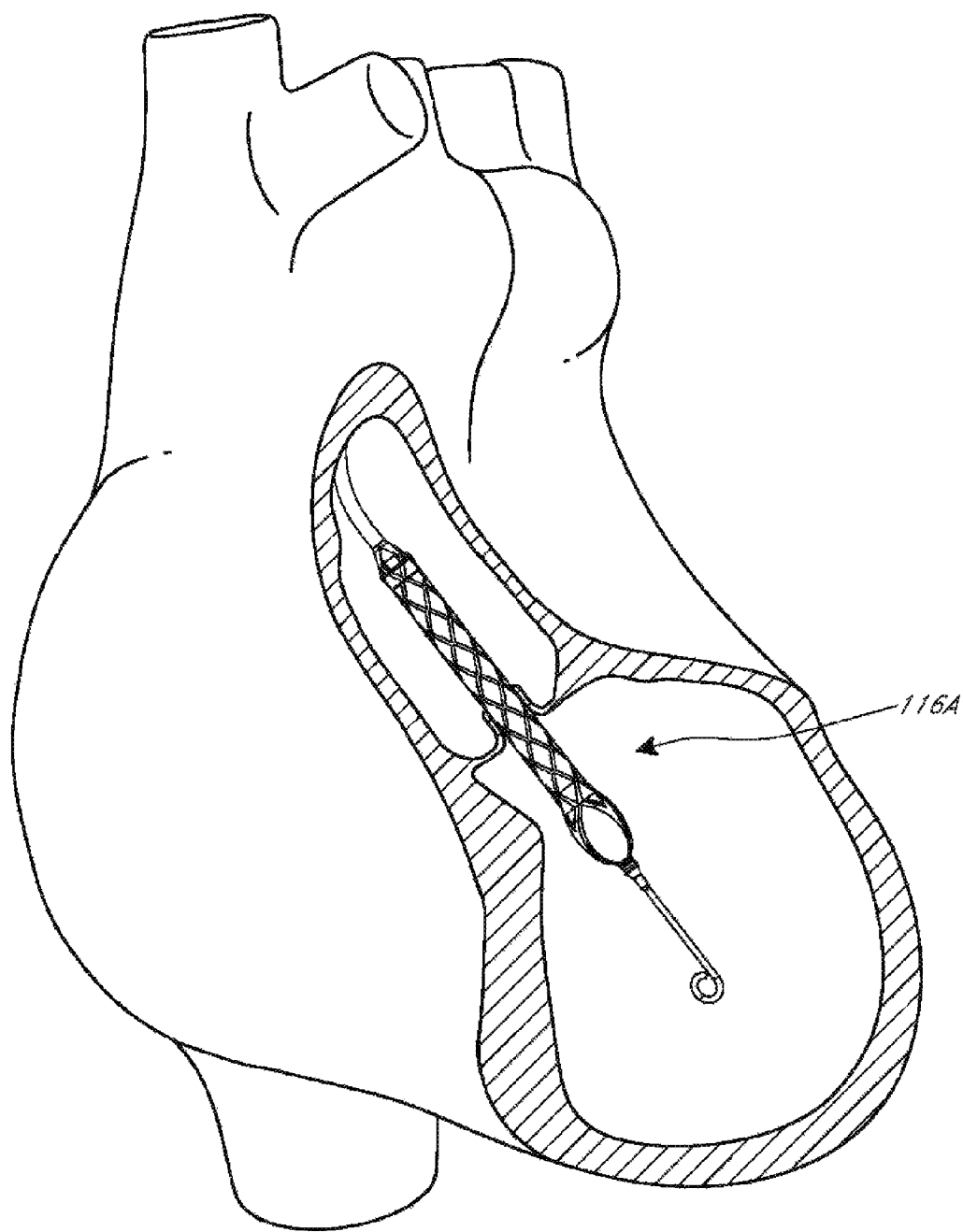
FIG. 1 is a schematic view of an operative device of a catheter assembly in position within the anatomy for assisting the left ventricle.

More detailed descriptions of various embodiments of components for heart pumps useful to treat patients experiencing cardiac stress, including acute heart failure, are set forth below.

DETAILED DESCRIPTION

This application is directed to fluid handling systems that are configured to control and/or manage fluid and electrical pathways in a catheter assembly, such as a catheter assembly of a percutaneous heart pump system. In particular, the disclosed percutaneous heart pump systems may include a catheter assembly and a console that includes a controller configured to control the fluid and electrical pathways that pass through the catheter assembly. Some of the disclosed embodiments generally relate to various configurations for coupling and engaging the catheter assembly with the console. For example, the console may be configured to control the flow rate of the pump and to monitor various physiological parameters and pump performance through the various electrical and fluid pathways of the catheter assembly. In some arrangements, the catheter assembly may be disposable, such that the catheter assembly can be discarded after use, while the console and controller are reusable. In embodiments with a reusable console and a disposable catheter assembly (or, indeed, in any embodiments where consoles and catheter assemblies may be coupled), it can be desirable to provide an effective interface between the catheter assembly and the console that completes the various fluid and electrical connections between the catheter assembly and the console.

In particular, it can be advantageous to provide an interface member at a proximal portion of the catheter assembly that is removably engageable with the console. Furthermore, to enhance usability and to minimize mistakes in making the connections, it can be important to make the interface easy to use so that users can easily connect the catheter assembly to the console before use and easily remove the catheter assembly from the console after use. Moreover, it can be important that the interface provides a secure connection between the interface member of the catheter assembly and an interface region of the console to ensure that the catheter assembly remains connected to the console uninterrupted during treatment.

As explained herein, one example of a catheter assembly is used in a percutaneous heart pump system having an operative device (e.g., an impeller assembly) that is configured to assist the patient's heart in pumping blood. The heart pump system may be configured to at least temporarily support the workload of the left ventricle in some embodiments. The exemplary heart pump can be designed for percutaneous entry through the femoral artery to a patient's heart. In particular, the exemplary impeller assembly can include a collapsible impeller and cannula, which can be inserted into the patient's vasculature at a catheter size of less than 13 FR, for example, about 12.5 FR in some arrangements. During insertion through the patient's vascular system to the heart, a sheath may maintain the impeller and cannula assembly in a stored configuration. When the impeller assembly is positioned in the left ventricle (or another chamber of a patient's heart), the impeller and cannula can expand to a larger diameter, for example to a catheter size of about 24 FR when the sheath is removed from the impeller assembly. The expanded diameter of the impeller and cannula may allow for the generation of higher flow rates, according to some embodiments.

For example, FIG. 1 illustrates one use of the disclosed catheter pump system. A distal portion of the pump, which can include an impeller assembly 116A, is placed in the left ventricle (LV) of the heart to pump blood from the LV into the aorta. The pump can be used in this way to treat patients with a wide range of conditions, including cardiogenic shock, myocardial infarction, and other cardiac conditions, and also to support a patient during a procedure such as percutaneous coronary intervention. One convenient manner of placement of the distal portion of the pump in the heart is by percutaneous access and delivery using the Seldinger technique, or other methods familiar to cardiologists. These approaches enable the pump to be used in emergency medicine, a catheter lab and in other non-surgical settings. Modifications can also enable the pump 10 to support the right side of the heart. Example modifications that could be used for right side support include providing delivery features and/or shaping a distal portion that is to be placed through at least one heart valve from the venous side, such as is discussed in U.S. Pat. No. 6,544,216; U.S. Pat. No. 7,070,555; and US 2012-0203056A1, all of which are hereby incorporated by reference herein in their entirety for all purposes.

Figure 2:
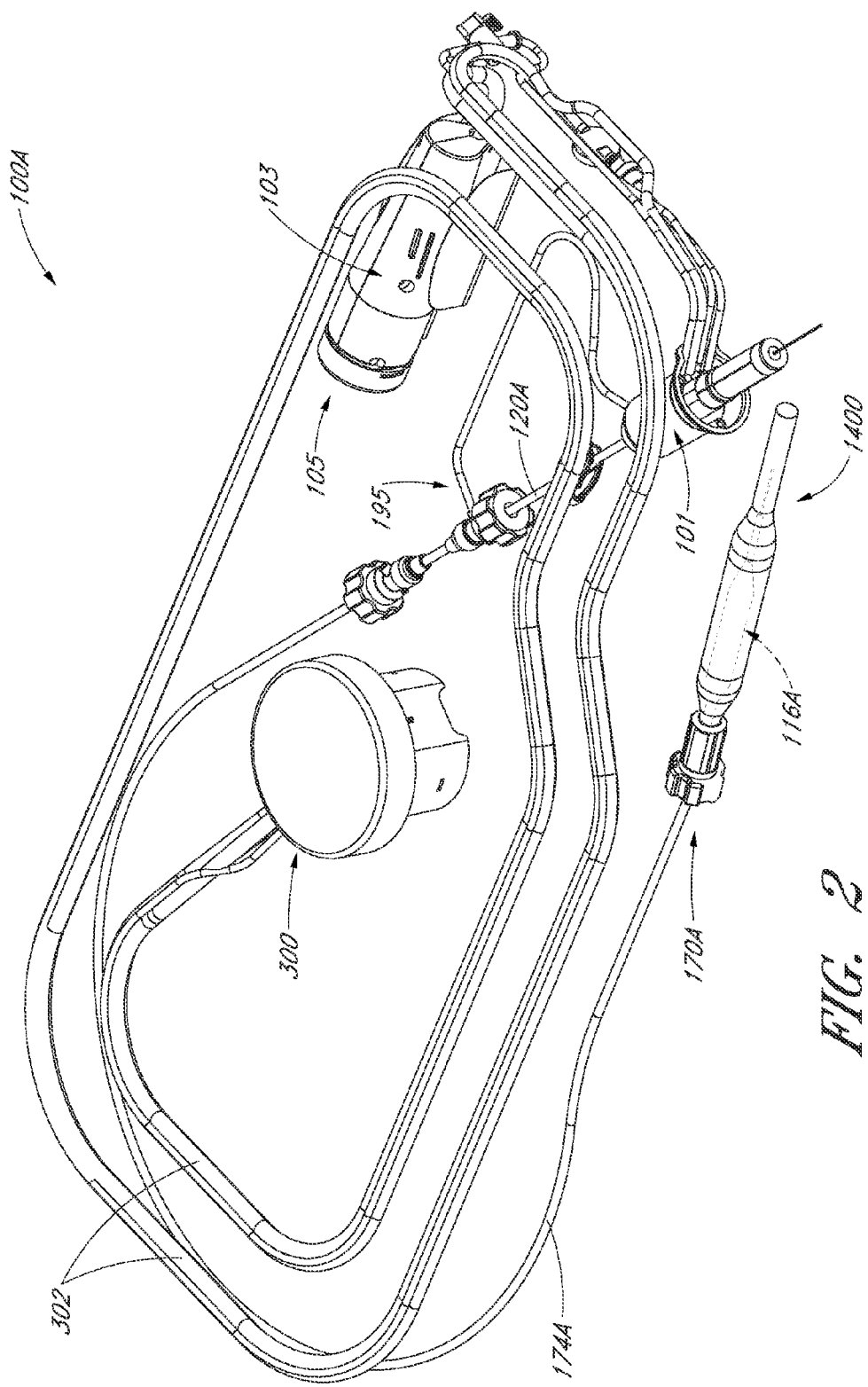
FIG. 2 is a three-dimensional perspective view of a catheter assembly, according to some embodiments.

Turning to FIG. 2, a three-dimensional perspective view of a catheter assembly 100A is disclosed. The catheter assembly 100A may correspond to the disposable portion of the heart pump systems described herein. For example, the catheter assembly 100A may include the impeller assembly 116A near a distal portion of the catheter assembly 100A, an elongate body 174A extending proximally from the impeller assembly 116A, an infusion system 195 configured to supply infusate to the catheter assembly 100A, a motor assembly comprising a driven assembly 101 and a drive assembly 103, one or more conduits 302 (e.g., electrical and/or fluid conduits) extending proximally from the motor assembly, and an interface member 300 coupled at a proximal portion of the conduits 302.

Moving from the distal end of the catheter assembly 100A of FIG. 2 to the proximal end, the impeller assembly 116A may be disposed at a distal portion of the catheter assembly 100A. As explained above, the impeller assembly 116A can include an expandable cannula or housing and an impeller with one or more blades. As the impeller rotates, blood can be pumped proximally (or distally in some implementations) to function as a cardiac assist device. A priming apparatus 1400 can be disposed over the impeller assembly 116A. As explained herein with reference to FIGS. 7-8, the priming apparatus 1400 can be configured to expedite a process of expelling air from the catheter assembly 100A before insertion of the operative device of the catheter assembly into the patient.

With continued reference to FIG. 2, the elongate body 174A extends proximally from the impeller assembly 116A to an infusion system 195 configured to allow infusate to enter the catheter assembly 100A and waste fluid to leave the catheter assembly 100A. A catheter body 120A (which also passes through the elongate body 174A) can extend proximally and couple to the driven assembly 101 of the motor assembly. The catheter body 120A can pass within the elongate body 174A, such that the elongate body 174A can axially translate relative to the catheter body 120A. Axial translation of the elongate body 174A relative to the catheter body 120A can enable the expansion and collapse of the impeller assembly 116A. For example, the impeller assembly 116A, coupled to a distal portion of the catheter body 120A, may expand into an expanded state by moving the elongate body 174A proximally relative to the impeller assembly 116A. The impeller assembly 116A may self-expand into the expanded state in some embodiments. In the expanded state, the impeller assembly 116A is able to pump blood at high flow rates. After the treatment procedure, the impeller assembly 116A may be compressed into a collapsed state by advancing a distal portion 170A of the elongate body 174A distally over the impeller assembly 116A to cause the impeller assembly 116A to collapse.

As explained above, the catheter body 120A can couple to the driven assembly 101 of the motor assembly. The driven assembly 101 can be configured to receive torque applied by the drive assembly 103, which is shown as being decoupled from the driven assembly 101 and the catheter assembly 100A in FIG. 2. The drive assembly 103 can be coupled to the driven assembly 101 by engaging a proximal portion of the driven assembly 101 with the drive assembly, e.g., by inserting the proximal portion of the driven assembly 101 into an aperture 105 of the drive assembly 103.

Although not shown in FIG. 2, a drive shaft can extend from the driven assembly 101 through the catheter body 120A to couple to an impeller shaft at or proximal to the impeller assembly 116A. The drive assembly 103 can electrically communicate with a controller in a console (see, e.g., FIGS. 3A-3B), which can be configured to control the operation of the motor assembly and the infusion system 195 that supplies a flow of infusate in the catheter assembly 100A. The impeller of the impeller assembly 116A may thus be rotated remotely by the motor assembly during operation of the catheter pump in various embodiments. For example, the motor assembly can be disposed outside the patient. In some embodiments, the motor assembly is separate from the controller or console, e.g., to be placed closer to the patient. In other embodiments, the motor assembly is part of the controller. In still other embodiments, the motor assembly is miniaturized to be insertable into the patient. Such embodiments allow the drive shaft to be much shorter, e.g., shorter than the distance from the aortic valve to the aortic arch (about 5 cm or less). Some examples of miniaturized motors catheter pumps and related components and methods are discussed in U.S. Pat. No. 5,964,694; U.S. Pat. No. 6,007,478; U.S. Pat. No. 6,178,922; and U.S. Pat. No. 6,176,848, all of which are hereby incorporated by reference herein in their entirety for all purposes.

As shown in FIG. 2, the motor assembly (e.g., the drive assembly 103 and the driven assembly 101) is in electrical communication with the controller and console by way of the conduits 302, which may include electrical wires. In particular, as shown in FIG. 2, the electrical wires may extend from the motor assembly proximally to the interface member 300. To enable the controller in the console to electrically communicate with the motor assembly and/or other sensors in the catheter assembly 100A (such as pressure sensors, flow sensors, temperature sensors, bubble detectors, etc.), it can be advantageous to provide a reliable electrical connection between the interface member 300 and the console. In various embodiments disclosed herein, therefore, the removable interface member 300 may include electrical components configured to couple to one or more electrical contacts (sometimes referred to herein as interconnections) in the console. The electrical connections may be achieved in a simple, user-friendly manner. In various embodiments disclosed herein, for example, the electrical connections may be made substantially at the same time, e.g., substantially simultaneously, as fluid connections are made between the interface member 300 and console. These and other structures incorporated to reduce the complexity of operating the pump system are provided to reduce the chance of errors in set-up and delays, which for the emergency conditions in which the pump may be implemented could be life-threatening.

The mechanical components rotatably supporting the impeller within the impeller assembly 116A permit high rotational speeds while controlling heat and particle generation that can come with high speeds. The infusion system 195 may deliver a cooling and lubricating solution to the distal portion of the catheter assembly 100A for these purposes. As shown in FIG. 2, the infusion system 195 may be in fluid communication with the interface member 300 by way of the conduits 302, which may also include fluid conduits or tubes. Because the catheter assembly 100A may be disposable and/or removable from a console, it can be important to securely couple interface member 300 to the console. Furthermore, it can be important to provide an easy-to-use interface such that users can easily complete fluid connections that remain secure during a treatment procedure. Maintaining security of the connection is important because the fluids and signals carried by the conduits 302 enable the impeller to operate in a continuous manner. Stoppage of the pump system may require the catheter assembly 100A to be removed from the patient and replaced in certain circumstances, which may be life-threatening or extremely inconvenient at a minimum.

When activated, the catheter pump system can effectively increase the flow of blood out of the heart and through the patient's vascular system. In various embodiments disclosed herein, the pump can be configured to produce a maximum flow rate (e.g. low mm Hg) of greater than 4 Lpm, greater than 4.5 Lpm, greater than 5 Lpm, greater than 5.5 Lpm, greater than 6 Lpm, greater than 6.5 Lpm, greater than 7 Lpm, greater than 7.5 Lpm, greater than 8 Lpm, greater than 9 Lpm, or greater than 10 Lpm. In various embodiments, the pump can be configured to produce an average flow rate at 62 mmHg pressure head of greater than 2 Lpm, greater than 2.5 Lpm, greater than 3 Lpm, greater than 3.5 Lpm, greater than 4 Lpm, greater than 4.25 Lpm, greater than 4.5 Lpm, greater than 5 Lpm, greater than 5.5 Lpm, or greater than 6 Lpm.

Various aspects of the pump and associated components are similar to those disclosed in U.S. Pat. Nos. 7,393,181; 8,376,707; 7,841,976; 7,022,100; and 7,998,054, and in U.S. Pub. Nos. 2011/0004046; 2012/0178986; 2012/0172655; 2012/0178985; and 2012/0004495, the entire contents of each of which are incorporated herein for all purposes by reference. In addition, this application incorporates by reference in its entirety and for all purposes the subject matter disclosed in each of the following concurrently filed applications: application Ser. No. 13/802,556, entitled "DISTAL BEARING SUPPORT," filed on Mar. 13, 2013; application Ser. No. 13/801,833, entitled "SHEATH SYSTEM FOR CATHETER PUMP," filed on Mar. 13, 2013; application Ser. No. 13/802,570, "IMPELLER FOR CATHETER PUMP," filed on Mar. 13, 2013; application Ser. No. 13/801,528, entitled "CATHETER PUMP," filed on Mar. 13, 2013; and application Ser. No. 13/802468, entitled "MOTOR ASSEMBLY FOR CATHETER PUMP," filed on Mar. 13, 2013.

Fluid Handling System

FIG. 3A is a three-dimensional perspective view of a fluid handling system 350 that includes a console 301 and the catheter assembly 100A of FIG. 2. The console 301 can provide electrical power, control signals, medical fluids (e.g., saline) for infusion, and fluid waste extraction to the catheter assembly 100A by way of its interface with the interface member 300. In this manner, a plurality of fluid connections can advantageously be made with a single interface. As illustrated in FIG. 2, for example, the removable interface member 300 may be disposed at a proximal portion of the catheter assembly 100A and may be configured to couple to the console 301 at an interface region 303.

In some embodiments, the fluid handling system 350 can be configured to deliver fluids to and/or remove fluids from the catheter assembly 100A. As discussed above and in the incorporated patent references, saline and/or other medical solutions can lubricate and/or cool component between the motor assembly and the operative device. If desired, waste fluids can be removed from the catheter assembly 100A using the fluid handling system 350. In some embodiments, the fluid handling system 350 can include a multilumen catheter body having a proximal end and a distal end. The catheter body can include one or more lumens through which medical solutions (e.g., saline), waste fluids, and/or blood can flow. To drive fluid through the catheter assembly 100A (e.g., into and/or out of the catheter assembly 100A), the console 301 may include one or more pump(s) configured to apply positive or negative pressure to the catheter assembly 100A when the catheter assembly 100A is coupled to the console 301 and engages the pump(s).

In addition, the fluid handling system 350 may also be configured to provide electrical communication between the console 301 and the catheter assembly 100A. For example, the console can include a controller (e.g., a processor) that is programmed to control and/or manage the operation of the motor assembly. The console 301 may also include electrical interfaces configured to supply power to the motor assembly and/or other components that are driven by electrical power when the interface member 300 is coupled to the console 301. Moreover, one or more electrical or electronic sensors may be provided in the catheter assembly 100A and may electrically couple to the console 301 by way of the fluid handling system 350. The embodiments disclosed herein may thereby provide fluid and electrical connections between the catheter assembly 100A and the console 301.

As explained above, the fluid handling system 350 may provide a removable interface between the catheter assembly 100A and the console 301, which may include various components, including, e.g., one or more pump(s), processors (e.g., the controller), electrical interconnections, etc. For example, to activate one or more pumps in the console 301 and/or to engage one or more electrical connections between the console 301 and the interface member 300, a user may simply insert a distal portion of the interface member 300 (e.g., including a closure member) along the illustrated Z-direction into an aperture 304 of the interface region 303 until the pump(s) are engaged and the electrical connection(s) are formed. In some aspects, the insertion of the interface member along the Z-direction may engage the pump(s) and complete the electrical connection(s) substantially simultaneously.

In some embodiments, the interface member 300 may be secured to the console 301 by engaging a locking device between the interface region 303 and the interface member 300. One convenient way to engage a locking device is by rotating a portion of the interface member 300 relative to another portion of the interface member or relative to the console 301, as explained herein. For example, rotation of an outermost structure (opposite the direction Z), sometimes referred to herein as a "cap" relative to the console may engage a locking mechanism configured to mechanically secure the interface member 300 to the console 301 to prevent the interface member 300 from being accidentally disengaged during a treatment procedure.

The console 301 may also include a user interface 312, which may comprise a display device and/or a touch-screen display. The user may operate the percutaneous heart pump system by interacting with the user interface 312 to select, e.g., desired flow rates and other treatment parameters. The user may also monitor properties of the procedure on the user interface 312.

FIG. 3B is a three-dimensional perspective view of the interface region 303 of the console 301 shown in FIG. 3A. The interface region 303 can include the aperture 304 configured to receive the distal portion of the interface member 303. The aperture 304 may include a generally circular cavity shaped and sized to receive a portion of the interface member 300. A bubble detector 308 (e.g., an optical sensor in some embodiments) can be positioned at a back wall of the aperture 304. The bubble detector 308 may include a recess portion defined by two walls sized and shaped to receive a segment of tubing. When fluid flows through the tubing (see, e.g., bubble detector tube segment 326 in FIG. 4), the bubble detector 308 may monitor the fluid to determine whether or not the fluid includes unwanted matter, e.g., bubbles of air or other gas. In some embodiments, the bubble detector 308 may measure the amount (number or volume) of bubbles in the fluid passing though the tube segment. It should be appreciated that it can be important to detect bubbles in the treatment fluid to avoid inducing embolisms in the patient. The bubble detector 308 may electrically communicate with the controller in the console 301 and can indicate the amount of bubbles in the treatment fluid. The console 301, in turn, can alert the user if there are bubbles in the treatment fluid.

The interface region 303 can also include one or more pumps, e.g., peristaltic pumps in some embodiments. The peristaltic pumps can be used to pump fluid into or out of the catheter assembly 100A to deliver medical fluids and to remove waste fluids, respectively. Such pumps may employ one or more rollers 306 to control delivery of a fluid within a respective tube (see, e.g., pump tube segments 324a, 324b of FIG. 4). For example, the one or more pump rollers 306 can be housed within the console 301. As shown, two pump rollers 306 are mounted about their rotational axes (e.g., the Y-direction illustrated in FIG. 3B) at the back wall of the aperture 304. The pump rollers 306 can be rotated by a peristaltic pump motor within the console (not shown in FIGS. 3A-3B). As explained in more detail herein with respect to FIG. 4 below, the rollers 306 can engage pump tube segments 324a, 324b to pump fluid into or out of the catheter assembly 100A. The pump rollers 306 may be configured to be received within occlusion bed regions of the interface member 300 (see, e.g., occlusion beds 322a and 322b of FIG. 4) to pump fluid through the catheter assembly 100A.

An electrical interconnect 307 can also be provided in the back wall of the aperture 304. The electrical interconnect 307 can be configured to provide power to the motor assembly and/or electrical signals or instructions to control the operation of the motor assembly. The electrical interconnect 307 can also be configured to receive electrical signals indicative of sensor readings for monitoring pressure, flow rates, and/or temperature of one or more components in the catheter assembly 100A. A recessed channel 309 can extend from the bottom of the aperture 304 along the side to the lower edge of the console 301. The recessed channel 309 can be shaped and sized to receive one or more of the conduits 302 (e.g., electrical and/or fluid conduits) extending between the interface member 300 and the motor assembly. In one embodiment, all of the conduits 302 can be received within the channel 309 providing a flush side surface when the interface member 300 is disposed in the interface aperture 304.

In addition, it can be important to ensure that the interface member 300 is controllably secured within the console 301 such that it is engaged and disengaged only when the user desires to engage or disengage the interface member 300 from the console 301. For example, as explained in more detail herein relative to FIGS. 5A-5C, the interface region 303 can include a groove 313 sized and shaped to receive a locking mechanism (e.g., a tab or flange projecting in the X direction) on the interface member 300. In one embodiment, a disengaging member 305 includes a spring-loaded release mechanism 310 provided above the aperture 304 and a pin 311 that can be inserted into a hole in the interface member 300 (see, e.g., FIGS. 5A-5C and the accompanying disclosure below). As explained below with respect to FIGS. 5A-5C, the pin 311 can assist in releasing the interface member 300 relative to the console 301. The spring-loaded release mechanism 310 can be pressed to release the pin 311 and unlock the interface member 300 from the console 301. As explained herein, the spring-loaded release mechanism 310 can therefore act as a further safety mechanism to ensure that the cassette is not accidentally disengaged by the user.

Removable Interface Member

Figure 4:
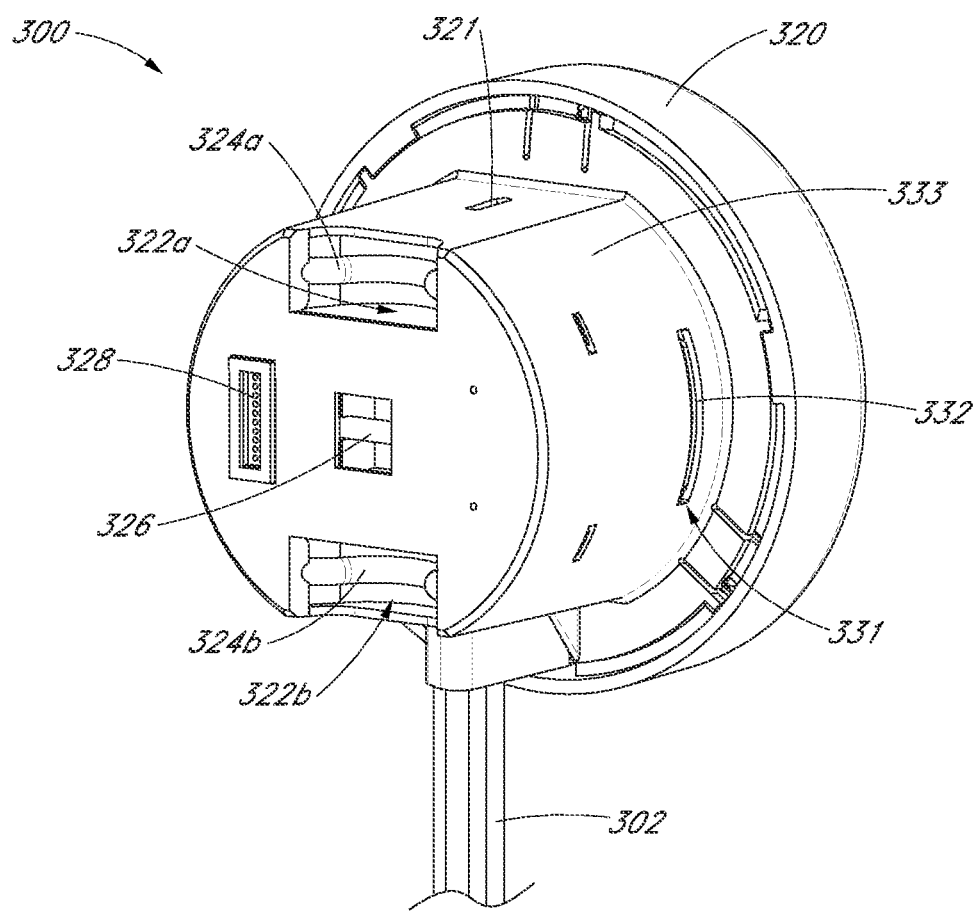
FIG. 4 is a three-dimensional perspective view of an interface member, according to one embodiment.

FIG. 4 is a three-dimensional perspective view of the interface member 300, according to one embodiment. The interface member 300 can comprise a body that is shaped and sized to fit into the interface region 303 of the console 301. As shown in FIG. 4, the interface member 300 can have a substantially circular profile, and is sometimes referred to as a puck. In some embodiments, the interface member 300 can include an outer body 333 operably coupled to a manual interface 320, sometimes referred to as a cap. The manual interface 320 is generally palm-sized so that a user can receive it in their hand and operate it comfortably, e.g., with finger pressure on the outer rim of the cap. One or more occlusion beds can be formed or provided at the interface between the interface member 300 and the console 301, e.g., in or on the interface member 300. For example, first and second occlusion beds 322a and 322b may be formed in the interface member 300. As shown in FIG. 4, for example, the occlusion beds 322a, 322b, can include arcuate recessed regions formed in the interface member 300.

The interface member 300 can further include first and second pump tube segments 324a, 324b positioned along the occlusion beds 322a, 322b formed in the interface member 300. When the interface member 300 is inserted into the console 301, the pump rollers 306 can engage with the interface member 300 and compress the tube segment(s) 324a, 324b against the occlusion bed(s) 322a, 322b, respectively. As the pump motor(s) in the console 301 rotate the rollers 306, fluid flows into uncompressed portions of the tube segment(s) 324a, 324b and continues flowing throughout the catheter assembly 100A. For example, by compressing the tube segments 324a, 324b, the fluid may be pumped into or out of the catheter assembly 100A by way of the conduits 302 extending from the interface member 300 to the motor assembly and distally beyond the motor assembly.

Figure 5A:
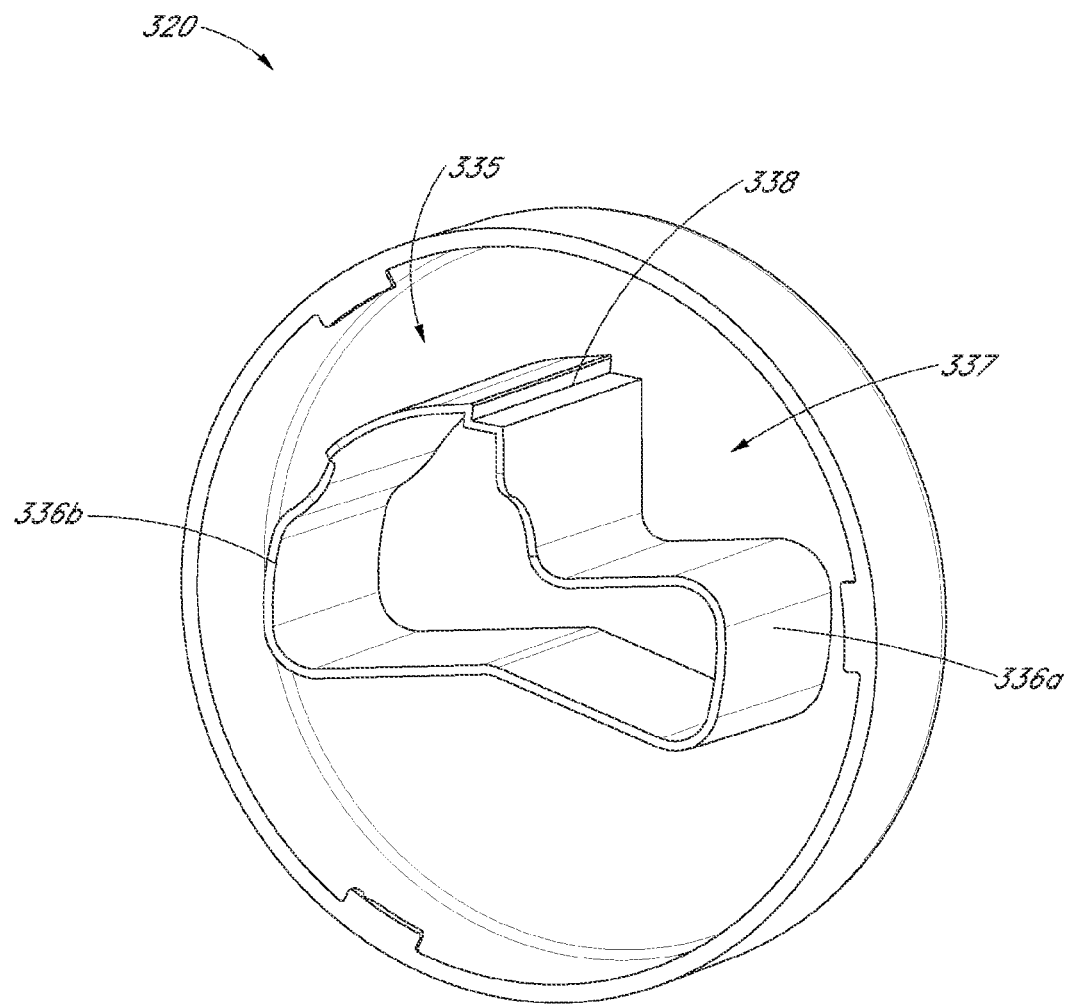
FIG. 5A is a three-dimensional perspective view of a cap.
Figure 5C:
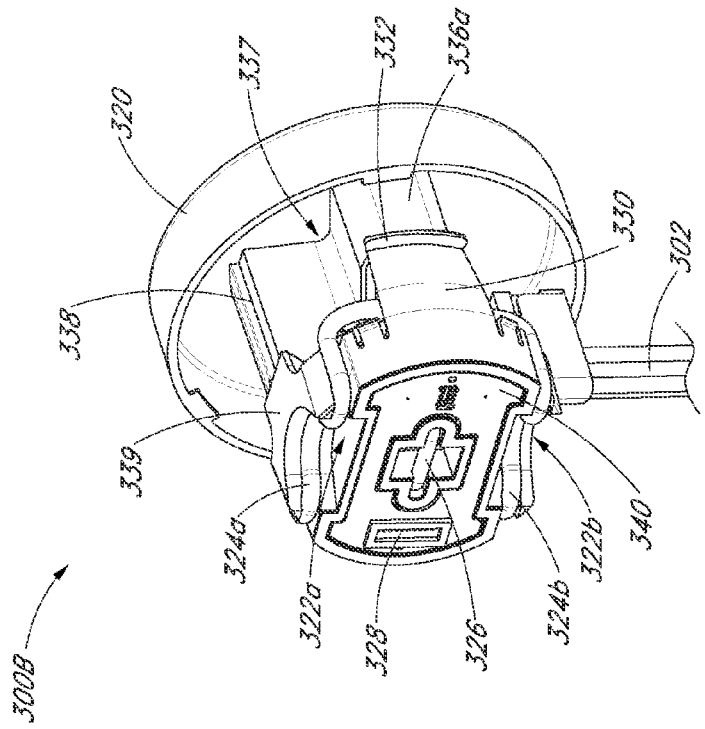
FIG. 5C is a three-dimensional perspective view of an interface member in a locked configuration.
Figure 5B:
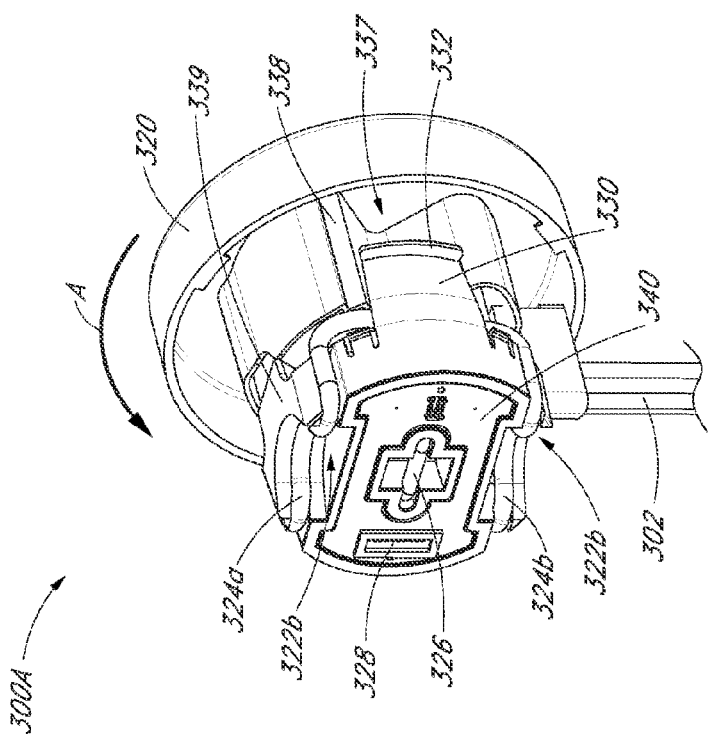
FIG. 5B is a three-dimensional perspective view of an interface member in an unlocked configuration.

Because the tolerances for the peristaltic pump can be rather tight, the body of the interface member 300 (e.g., the outer body 333 and/or an inner body, such as inner body 339 illustrated in FIGS. 5B-5C) can be formed with precise tolerances (e.g., molded from a unitary structure in some implementations) such that when the interface member 300 is inserted into the console 301, the pump rollers 306 precisely and automatically engage with the tube segments 324a, 324b and occlusion beds 322a, 322b to reliably occlude the tube segments 324a, 324b and pump fluids through the catheter assembly 100A. Thus, when the interface member 300 is inserted sufficiently far into the interface region 303, the pump in the console 301 can automatically engage the interface member 300.

For example, the gap between the rollers 306 and the occlusion beds 322a, 322b can be less than about two wall thicknesses of the tube segments 324a, 324b in some arrangements, such that the tubes 324a, 324b can be effectively occluded. Due to the precise tolerances of the interface member 300, the pump can be engaged by simply inserting the interface member 300 into the console 301. There is no need to separately activate the pump in some embodiments. The dimensions of the interface member 300 may be selected such that the occlusion bed(s) 322a, 322b automatically engages the respective pump rollers 306 upon insertion of the interface member 300 into the console 301.

The above configuration provides several advantages. As one of skill in the art will appreciate from the description herein, the interface member 300 and interface region 303 provide an easy-to-use, quick connection of the tubing segments to one or more respective rollers 306. Moreover, the components can be manufactured easily and cost-effectively because only certain components require tight tolerances and the interface of member 300 to region 303 is essentially self-aligning. The interface also eliminates any need to engage the pump through a second mechanism or operator step, streamlining operation of the heart pump and simplifying the engagement of the catheter assembly 100A to the console 301. Also, in implementations where the console 301 is mounted on an IV pole with rollers, or another type of lightweight cart, for example, the simplified engagement mechanisms disclosed herein can be advantageous because there is only a minimal applied force against the pole, which prevents the pole from rolling or tipping when the pump is engaged.

The pump tube segments 324a, 324b can be mounted on the interface body 300 near or in the respective occlusion beds 322a, 322b. As illustrated, the first and second pump tube segments 324a, 324b can be configured to engage with the pump rollers 306 in the console 301, as explained above. The first and second pump tube segments 324a, 324b can have an arcuate shape (which may be pre-formed in various arrangements) that generally conforms to the curved shape of each respective occlusion bed 322a, 322b. The pump rollers 306 within the console 301 can thereby be positioned within the occlusion beds 322a, 322b to compress the tube segments 324a, 324b against the wall of the occlusion beds 322a, 322b. In addition, a bubble detector tube segment 326 can also be mounted in or on the interface member 300 and can be configured to engage with or be positioned adjacent to the bubble detector 308 illustrated in FIG. 3B. The bubble detector tube segment 326 can be any suitable shape. As illustrated, the bubble detector tube segment can be substantially straight and can be sized and shaped to be received by the bubble detector 308 within the console 301. As explained above with respect to FIGS. 3A-3B, the bubble detector 308 (which may be an optical sensor) can be used to detect air bubbles in the treatment or lubricating fluid being supplied to the patient.

The tube segments can be fluidly connected to the remainder of the catheter assembly 100A, including, e.g., one or more lumens of the catheter body, by way of the conduits 302. In operation, therefore, the removable interface member 300 may allow fluid to be pumped into and out of the patient within a controlled system, e.g., such that the fluids within the catheter assembly 100A can be pumped while maintaining a sterile environment for the fluids. Depending on the implementation, the volume of medical solution into the catheter body can be equal to, or can exceed by a minimum amount, the volume of medical solution out of the catheter body to assure that blood does not enter a blood-free portion of the heart pump.

In addition, one or more electrical contacts 328 can be provided in the interface member 300. The electrical contacts 328 can be any suitable electrical interface configured to transmit electrical signals between the console 301 and the catheter assembly 100A (e.g., the motor assembly and/or any suitable sensors). For example, the electrical contacts 328 can be configured to electrically couple to the electrical interconnect 307 disposed in the console 301. Electrical control signals and/or power may be transmitted between the console 301 and the catheter assembly 100A by way of the electrical connection between the electrical contacts 328 and the electrical interconnect 307. Advantageously, the electrical connection between the electrical contacts 328 and the electrical interconnect 307 may be formed or completed when the interface member 300 is inserted into the interface region 303 of the console 301. For example, in some embodiments, the electrical connection between the electrical contacts 328 and the electrical interconnect 307 may be formed substantially simultaneously with the fluid connection (e.g., the engagement of the pump) when the interface member 300 is inserted into the interface region 303. In some aspects, for example, the electrical connection can be formed by inserting electrical pins from the electrical contacts 328 into corresponding holes of the electrical interconnect 307 of the console 301, or vice versa.

Further, as shown in FIG. 4, the manual interface 320 can be mechanically coupled to a proximal portion of the outer body 333 and may be configured to rotate relative to the outer body 333 in a constrained manner, as explained below relative to FIGS. 5A-5C. For example, the outer body 333 can include one or more locking apertures 331 configured to receive locking tabs 332 that are configured to lock the manual interface 320 relative to the console 301. Moreover, as explained below relative to FIGS. 5A-5C, the outer body 333 may include a pin hole 321 sized and shaped to receive the pin 311 illustrated in FIG. 3B to releasably couple the removable interface member 300 relative to the console 301.

One will appreciate from the description herein that the configuration of the pump rollers, occlusion bed, and tubing can be modified depending on the application in accordance with the present inventions. For example, the configuration may be modified to provide easier access for service and repair. In various embodiments, the pump rollers may be disposed external to the console. In various embodiments, the pump rollers and occlusion bed may be both disposed within the cassette. In various embodiments, the console includes a mechanism to actuate the pump rollers in the cassette. In various embodiments, the rollers may be fixed. In various embodiments, the rollers may be configured to rotate, translate, or both. The rollers and/or the occlusion bed may be positioned on a base that is configured to move. In some embodiments, the console-cassette interface can include a positive pressure interface to pump fluid (e.g., saline) into the patient's vasculature and a negative pressure interface to pump fluid (e.g., waste fluid) out of the patient's vasculature.

Locking Mechanism

As discussed above, the interface member 300 advantageously can be fully engaged with the console 301 by simply inserting it into a correspondingly shaped aperture 304 in the housing of the console 301. When interface member 300 is brought into adjacency with a back wall of the interface region 303 of the console, e.g., when the interface member 300 is inserted into the aperture 304, the fluid handling and electrical connections are made, and the system 350 is operational. A locking mechanism in the interface member 300 can be provided for additional security, which can be particularly useful for patient transport and other more dynamic settings. For example, it is desirable to ensure that the catheter assembly 100A is secured to the console 301 during the entire procedure to ensure that the procedure is not disrupted due to accidental disengagement of the interface member 300 from the console 301.

In one embodiment, the locking mechanism can be disposed between the console 301 and the interface member 300 and can be configured to be engaged by a minimal movement of an actuator. For example, the manual interface 320 can be provided to cause engagement of a locking device by a small rotational turn of the manual interface 320 relative to the console 301.

FIG. 5A is a three-dimensional perspective view of the manual interface 320. As shown in FIG. 5A, the manual interface 320 can include or be coupled with an internal cam 335. The cam 335 can include one or more protruding lobes, such as lobes 336a and 336b. Further, the cam 335 can include a recessed region 337 recessed inwardly relative to the lobes 336a, 336b. The cam 335 can also include a stepped region 338 which can enable the interface member 300 to be locked and unlocked relative to the console 301, as explained herein.

FIG. 5B is a three-dimensional perspective view of an interface member 300A in an unlocked configuration, and FIG. 5C is a three-dimensional perspective view of an interface member 300B in a locked configuration. It should be appreciated that the interface members 300A, 300B of FIGS. 5B and 5C are illustrated without the outer body 333, which has been hidden in FIGS. 5B and 5C for purposes of illustration. Unless otherwise noted, the components of FIGS. 5B and 5C are the same as or similar to the components illustrated with respect to FIG. 4. As shown in FIGS. 5B and 5C, the interface members 300A, 300B can include an inner body 339 that can be disposed within the outer body 333 shown in FIG. 4. The occlusion beds 322a, 322b can be formed in the inner body 339 of the interface member 300A, 300B, as shown in FIGS. 5B-5C; however, in other arrangements, the occlusion beds 322a, 322b may be formed in the outer body 333 or other portions of the interface member 300A, 300B. In addition, as shown in FIGS. 5A and 5B, an electrical component 340 can be disposed in a recess or other portion of the inner body 339. Additional details regarding the electrical component 340 are explained below with respect to FIGS. 6A-6B.

The inner body 339 of the interface member 300A, 300B can further include a protrusion 330 that includes the tab 332 at a distal portion of the protrusion 330. When the interface member 300A is in the unlocked configuration, the protrusion 330 can be disposed in or near the recess 337 of the cam 335 in the manual interface 320. The cam 335 may therefore not contact or apply a force against the protrusion 330 when the interface member 300A is in the unlocked configuration, as shown in FIG. 5B.

However, once the interface member 300 is inserted into the console 301, the interface member 300 can be locked into place by rotating the manual interface 320 relative to the inner body 339 and the console 301, e.g., rotated in the A-direction illustrated in FIG. 5B. When the manual interface 320 is rotated, the internal cam 335 is also rotated within the interface member 300A, 300B. Once the cam is rotated, the lobes 336a, 336b of the cam 335 can engage with the one or more protrusions 330 of the inner body 339 and can push the protrusions 330 outwardly relative to the inner body 339. In one embodiment, the tabs 332 may extend outwardly through the locking apertures 331 formed on the outer body 333. When the tab(s) 332 are pushed through the locking aperture(s) 331, the tabs 332 project laterally outward from the outer body 333. In this position, in some embodiments, each of the tabs 332 can lock into the groove(s) 313 in the console 301 (see FIG. 3B) to secure the interface member 300B to the console 301. Thus, in the unlocked position, the tab 332 can be substantially flush with the outer surface of the interface member 300A, and in the locked position, the tab 332 can extend through the locking aperture 331 and lock into the grooves 313 in the console 301.

In some embodiments, the protrusion 330 can be a cantilevered protrusion from the inner body 339. As mentioned above, it can be important to maintain tight tolerances between the occlusion beds 322a, 322b, which is also formed in the interface member, and the pump rollers 306 when the interface member 300 engages with the console 301. Because the occlusion beds 322a, 322b may be formed in the same body as the cantilevered protrusions 330, conventional manufacturing processes, such as molding processes, can be used to manufacture the interface member 300 (e.g., the outer body 333 and/or the inner body 339) according to precise dimensions. Thus, the protrusion(s) 330, tab(s) 332 and the occlusion bed(s) 322a, 322b can be made within tight dimensional tolerances, and the tab(s) 332 and/or protrusion(s) 330 can be positioned relative to the occlusion bed(s) 322a, 322b with very high precision such that when the interface member 300 is engaged with the console 301, the tube segments 324a, 324b are optimally occluded. Moreover, because the interface member 300 can be locked by rotating the manual interface 320 on the interface member 300, only minimal forces are applied to the console 301. This enhances the advantages of minimizing disruption of a mobile cart or IV pole to which the system may be coupled.

Disengagement Mechanism

It can also be important to provide a disengagement mechanism configured to decouple the interface member 300 from the console 301. With reference to FIGS. 3B, 4, 5B, and 5C, the disengaging member 305 of the console 301 can be configured to disengage and unlock the interface member 300 from the console 301. For example, the pin 311 may be spring-loaded such that when the interface member 300A is in the unlocked configuration, the pin 311 extends through the pin hole 321 of the outer body 333 but only contacts a side surface of one of the lobes 336b of the cam 335. Thus, in the unlocked configuration of the interface member 300A, the pin 311 may simply slide along the cam surface, permitting rotation of the manual interface 320 relative to the pin 311 and the console 301.

As shown in FIGS. 3B and 5C, however, when the interface member 300B is rotated into a locked configuration, the pin 311 can engage with the stepped region 338 of the internal cam 335, e.g., the spring-biased pin 311 can extend into the stepped region 338 or shoulder of the cam 335. By engaging the stepped region 338, the pin 311 prevents the cam 335 from rotating from the locked configuration to the unlocked configuration. A user can disengage the cassette by pressing the spring-loaded release mechanism 310 to release the spring and remove the pin 311 from the stepped region 338. The pin 311 can thereby be disengaged from the stepped region 338, and the internal cam 335 can rotate back into the unlocked position. When the cam 335 is moved back into the unlocked position, the tab 332 can be withdrawn from the groove 313 in the console 301 to unlock the interface member 300.

Electrical Interconnections, Components, and Cables

Figure 6A:
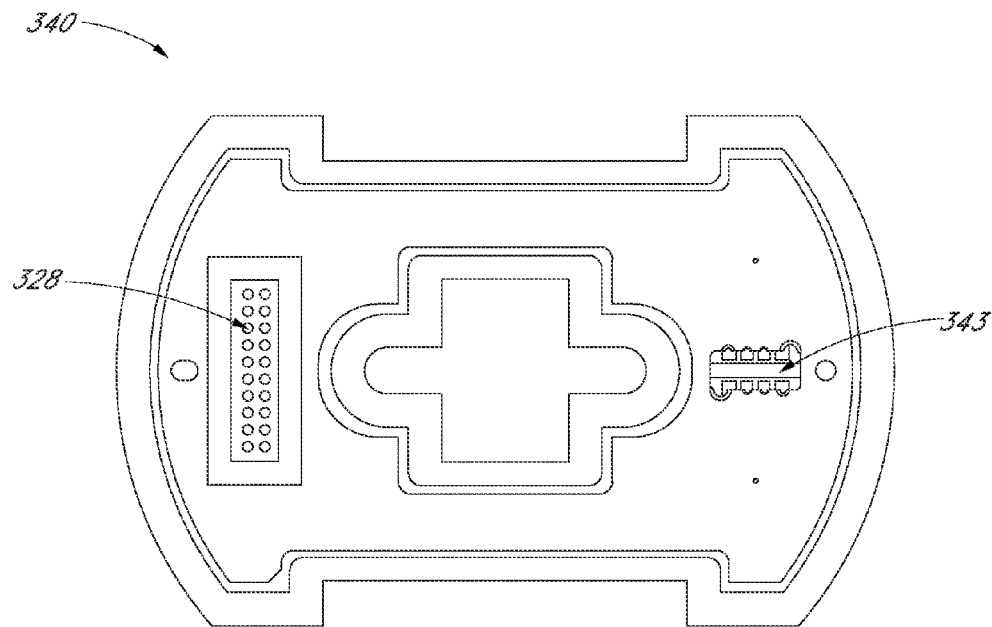
FIG. 6A is a three-dimensional perspective view of a first side of an electrical component, according to one embodiment.
Figure 6B:
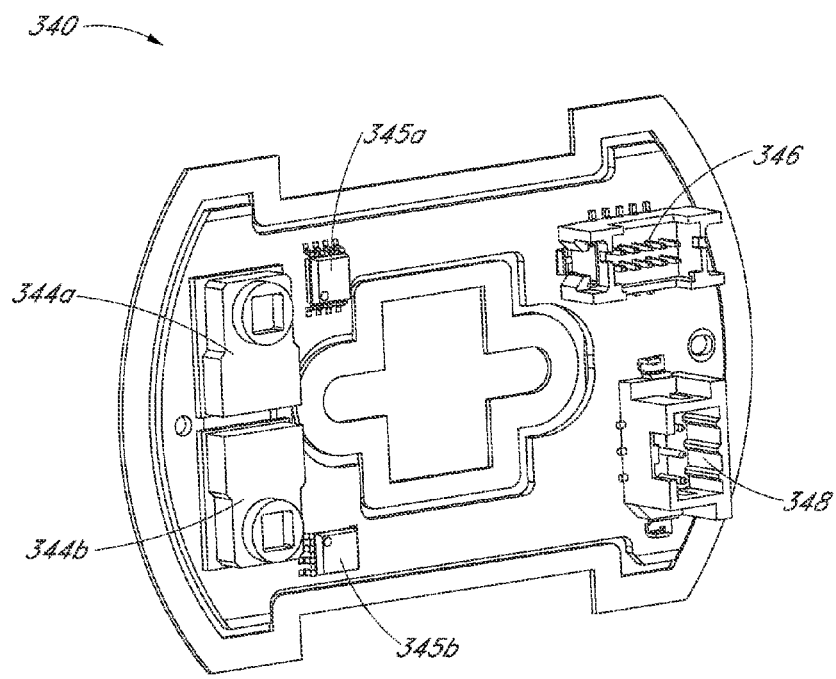
FIG. 6B is a three-dimensional perspective view of a second, opposite side of the electrical component of FIG. 6A.

FIG. 6A is a three-dimensional perspective view of a first side of the electrical component 340 illustrated in FIG. 4. FIG. 6B is a three-dimensional perspective view of a second, opposite side of the electrical component 340 of FIG. 6A. As shown in FIGS. 5B-5C, the electrical component 340 may be disposed in a recess of the interface member 300. The electrical component 340 can be any suitable electrical or electronic component, including, e.g., a printed circuit board (PCB) configured to provide an electrical interface between various components in the catheter assembly 100A and the console 301. As explained herein, the electrical component 340 can form an electrical interface between the interface member 300 and the console 301 to provide electrical communication between the console 301 and the catheter assembly 100A (such as the motor assembly and/or various sensors).

For example, the electrical component 340 of the interface member 300 can include the one or more electrical contacts 328 configured to mate with the corresponding electrical interconnect 307 in the console 301. The electrical contacts 328 and/or the electrical interconnect 307 can be, for example, nine-pin electrical interconnects, although any suitable interconnect can be used. The motor assembly that drives the operative device (e.g., impeller) of the catheter pump can be electrically connected to the interface member 300 by way of one or more electrical cables, e.g., the conduits 302. In turn, the console 301 can be coupled to a power source, which can drive the catheter pump motor assembly by way of the interface member's contacts 328 and the electrical conduits 302 connecting the interface member 300 to the motor assembly. The electrical component 340 can also include communications interconnects configured to relay electrical signals between the console 301 and the catheter pump motor assembly or other portions of the catheter assembly 100A. For example, a controller within the console 301 (or interface member) can send instructions to the catheter pump motor assembly via the electrical component 340 between the console 301 and the interface member 300. In some embodiments, the electrical component 340 can include interconnects for sensors (such as pressure or temperature sensors) within the catheter assembly 100A, including sensors at the operative device. The sensors may be used to measure a characteristic of the fluid in one or more of the tubes (e.g., saline pressure). The sensors may be used to measure an operational parameter of the system (e.g., ventricular or aortic pressure). The sensors may be provided as part of an adjunctive therapy.

The electrical component 340 within the interface member 300 can be used to electrically couple the cable (and the motor assembly, sensors, etc.) with the corresponding interconnects 307 in the console 301. For example, one or more internal connectors 346 and 348 on the second side of the electrical component 340 may provide electrical communication between the contacts 328 (configured to couple to the interconnects 307 of the console 301) and the catheter assembly 100. For example, electrical cables (e.g., the conduits 302) can couple to a first internal connector 346 and a second internal connector 348. The internal connectors 346, 348 may electrically communicate with the contacts 328 on the first side of the electrical component 340, which in turn communicate with the interconnects 307 of the console 301.

In various embodiments, the electrical component 340 is fluidly sealed to prevent the internal electronics from getting wet. This may be advantageous in wet and/or sterile environments. This may also advantageously protect the electronics in the event one of the fluid tubes leaks or bursts, which is a potential risk in high pressure applications.

In addition, the electrical component 340 (e.g., PCB) can include various electrical or electronic components mounted thereon. As shown in FIG. 6B, for example, two pressure sensors 344a, 344b can be mounted on the electrical component 340 to detect the pressure in the pump tube segments 324a, 324b. The pressure sensors 344a, 344b may be used to monitor the flow of fluids in the tube segments 324a, 324b to confirm proper operation of the heart pump, for example, confirming a proper balance of medical solution into the catheter body and waste out of the catheter body. Various other components, such as a processor, memory, or an Application-Specific Integrated Circuit (ASIC), can be provided on the circuit board. For example, respective pressure sensor ASICs 345a, 345b can be coupled to the pressure sensors 344a, 344b to process the signals detected by the pressure sensors 344a, 344b. The processed signals may be transmitted from the ASICs 345a, 345b to the console 301 by way of internal traces (not shown) in the PCB and the contacts 328.

Priming and Infusate System and Apparatus

Figure 7:
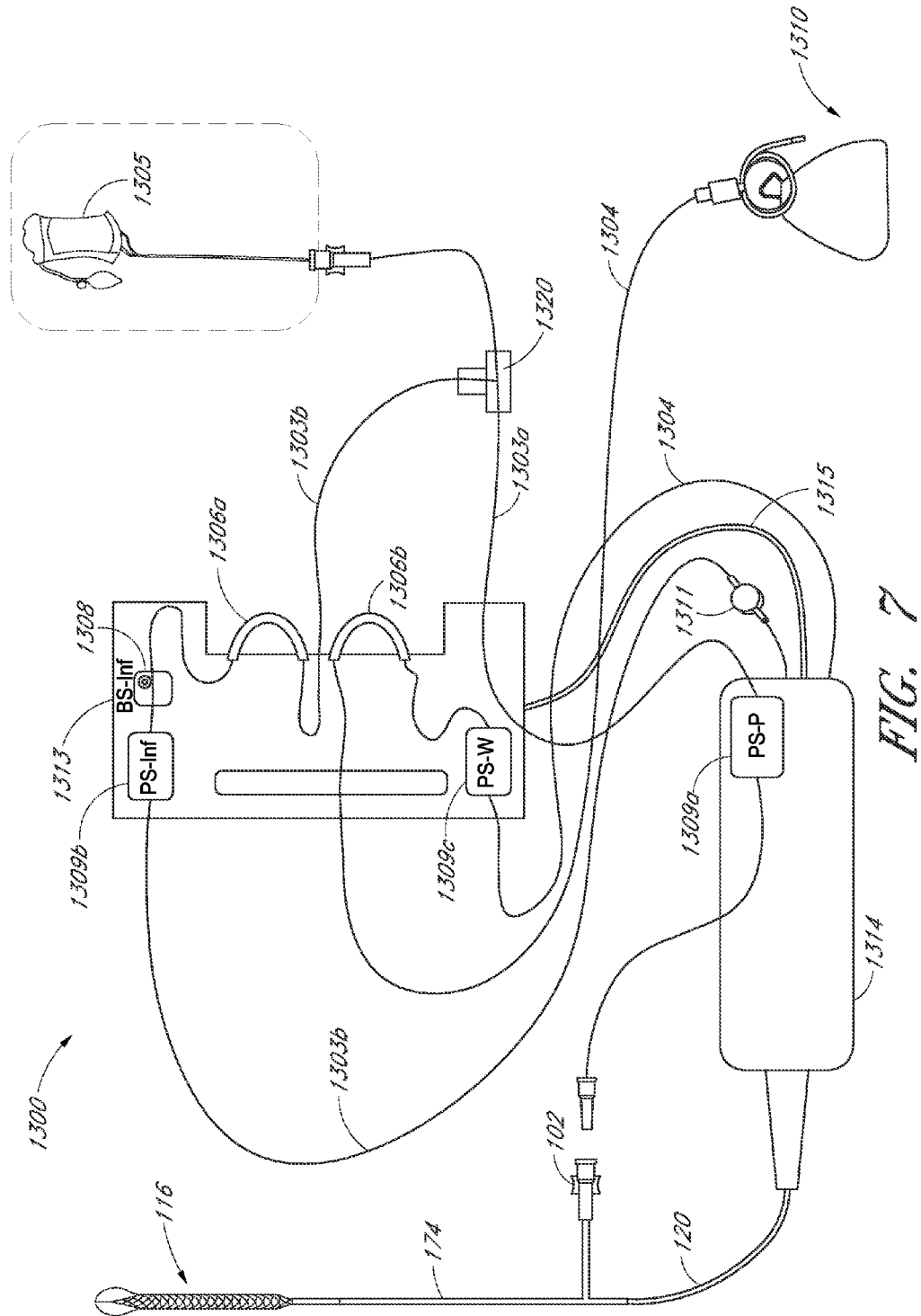
FIG. 7 is a schematic diagram of an infusate system, according to one embodiment.

One embodiment of an infusate system 1300 is illustrated in FIG. 7. Various components described herein can be understood in more detail by referencing the patent applications incorporated by reference herein. The infusate system 1300 can be configured to supply treatment and/or lubricating fluids to the operative device of the catheter assembly (e.g., an impeller assembly 116), and to remove waste fluid from the assembly. Furthermore, as explained herein, an elongate body 174 can be slidably disposed over a catheter body 120, such that there may be gaps or channels between the outer surface of the catheter body 120 and the inner surface of the elongate body 174. Such gaps or channels can contain air pockets harmful to the patient during a medical procedure. In addition, the lumen or lumens extending within the catheter body 120 also can contain air pockets harmful to the patient. Thus, it is desirable to expel air from both the lumens within catheter body 120 and the gaps or channels disposed between the elongate body 174 and the catheter body 120 before conducting a treatment procedure.

The system 1300 of FIG. 7 may be configured to supply fluid to the catheter assembly during treatment, to remove waste fluid during treatment, and/or to expel air from the elongate body 174, e.g., between the inner surface of the elongate body 174 and the outer surface of the catheter body 120 before treatment. In this embodiment, an interface member 1313 (similar to or the same as the interface member 300 described herein, in some aspects) may be provided to connect various components of the catheter assembly, as discussed herein. An outer sheath tubing 1303a can extend from a fluid reservoir 1305 to a luer 102 configured to be coupled to an infusate device. As shown in FIG. 7, the outer sheath tubing 1303a can be configured to deliver fluid to the outer sheath, e.g., the space between the elongate body 174 and the catheter body 120. The fluid reservoir 1305 may optionally include a pressure cuff to urge fluid through the outer sheath tubing 1303a. Pressure cuffs may be particularly useful in fluid delivery embodiments using gravity-induced fluid flow. The luer 102 can be configured to deliver infusate or other priming fluid to the elongate body 174 to expel air from the elongate body 174 as described herein in order to "prime" the system 1300. In addition, a pressure sensor 1309a, which may be disposed on a motor housing 1314, can be coupled to the outer sheath tubing 1303a to measure the pressure of the infusate or priming fluid flowing through the outer sheath tubing 1303a and into the luer 102. The motor housing 1314 illustrated in FIG. 7 may be the same as or similar to the motor assembly described above with reference to FIG. 2, for example, when the drive assembly 103 is coupled to the driven assembly 101.

As illustrated in the embodiment of FIG. 7, inner catheter tubing 1303b can extend between the motor housing 1314 and the fluid reservoir 1305, by way of a T-junction 1320. The inner catheter tubing 1303b can be configured to deliver fluid to the lumen or lumens within catheter body 120 during treatment and/or to expel air from the catheter 120 and prime the system 1300. A pumping mechanism 1306a, such as a roller pump for example, can be provided along inner catheter tubing 1303b to assist in pumping the infusate or priming fluid through the system 1300. As explained herein, the roller pump can be a peristaltic pump in some arrangements. In addition, an air detector 1308 can be coupled to the inner catheter tubing 1303b and can be configured to detect any air or bubbles introduced into the system 1300. In some embodiments, a pressure sensor 1309b can couple to inner catheter tubing 1303b to detect the pressure of the fluid within the tubing. Additionally, a filter 1311 can be employed to remove debris and other undesirable particles from the infusate or priming fluid before the catheter body 120 is infused or primed with liquid. In some embodiments, the air detector 1308, the pressure sensor 1309b, and the pumping mechanism 1306a can be coupled to the interface member 1313 described above (such as the interface member 300). One or more electrical lines 1315 can connect the motor housing 1314 with the cassette 1313. The electrical lines 1315 can provide electrical signals for energizing a motor or for powering the sensor 1309a or for other components. To expel air from the catheter body 120, infusate or priming fluid can be introduced at the proximal end of the catheter assembly. The fluid can be driven distally to drive air out of the catheter body 120 to prime the system.

In some aspects, a waste fluid line 1304 can fluidly connect the catheter body 120 with a waste reservoir 1310. A pressure sensor 1309c, which may be disposed on or coupled to the interface member 1313, can measure the pressure of the fluid within the waste fluid line 1304. A pumping mechanism 1306b, such as a roller pump, for example, can be coupled to the interface member 1313 and can pump the waste fluid through the waste fluid line 1304 to the waste reservoir 1310.

Figure 8:
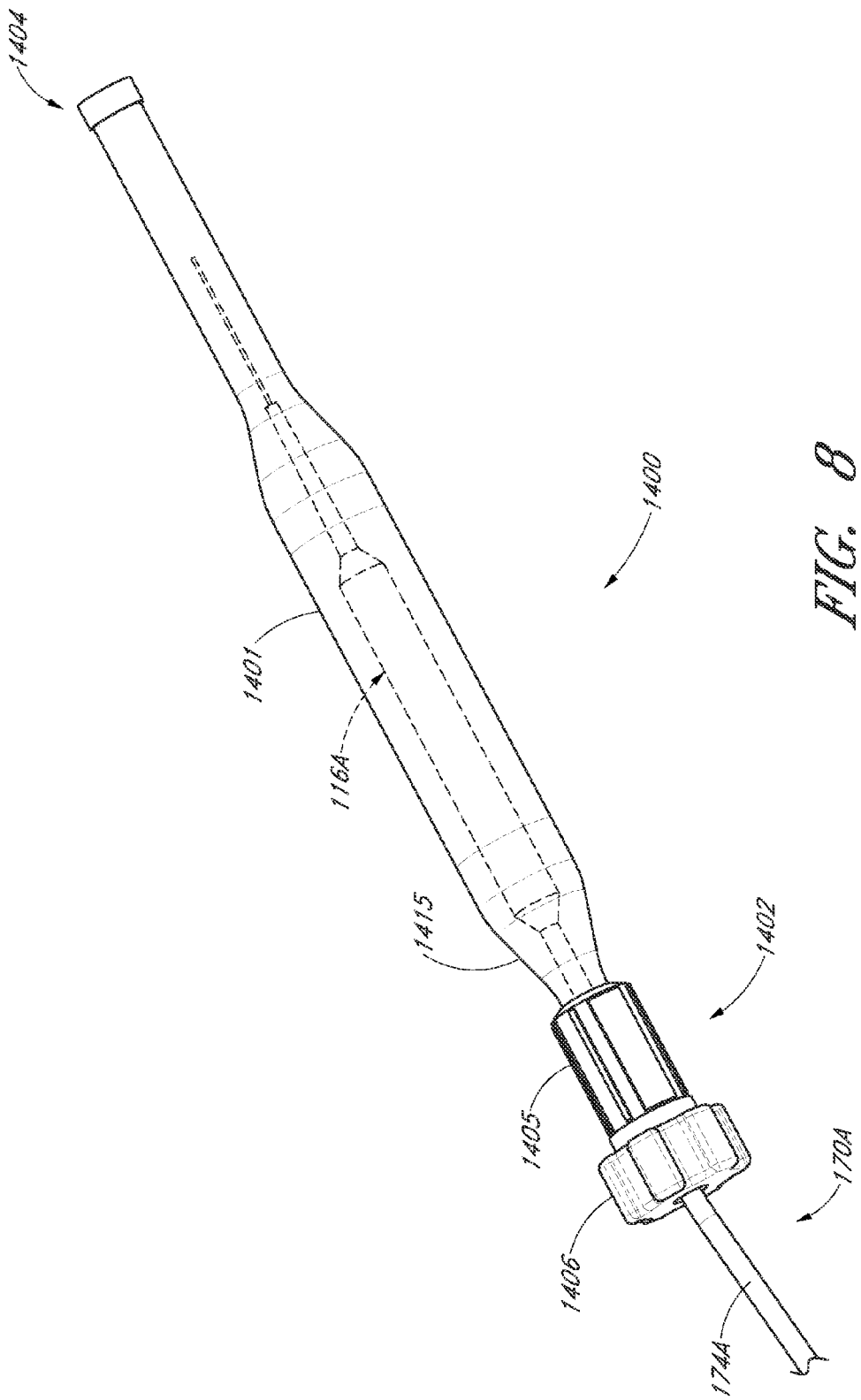
FIG. 8 is an enlarged view of a priming apparatus shown in FIG. 2.

FIG. 8 is an enlarged view of the priming apparatus 1400 shown in FIG. 2. As explained above, the priming apparatus 1400 may be disposed over the impeller assembly 116A near the distal end 170A of the elongate body 174A. The priming apparatus 1400 can be used in connection with a procedure to expel air from the impeller assembly 116A, e.g., any air that is trapped within the housing or that remains within the elongate body 174A near the distal end 170A. For example, the priming procedure may be performed before the pump is inserted into the patient's vascular system, so that air bubbles are not allowed to enter and/or injure the patient. The priming apparatus 1400 can include a primer housing 1401 configured to be disposed around both the elongate body 174A and the impeller assembly 116A. A sealing cap 1406 can be applied to the proximal end 1402 of the primer housing 1401 to substantially seal the priming apparatus 1400 for priming, i.e., so that air does not proximally enter the elongate body 174A and also so that priming fluid does not flow out of the proximal end of the housing 1401. The sealing cap 1406 can couple to the primer housing 1401 in any way known to a skilled artisan. However, in some embodiments, the sealing cap 1406 is threaded onto the primer housing by way of a threaded connector 1405 located at the proximal end 1402 of the primer housing 1401. The sealing cap 1406 can include a sealing recess disposed at the distal end of the sealing cap 1406. The sealing recess can be configured to allow the elongate body 174A to pass through the sealing cap 1406.

The priming operation can proceed by introducing fluid into the sealed priming apparatus 1400 to expel air from the impeller assembly 116A and the elongate body 174A. Fluid can be introduced into the priming apparatus 1400 in a variety of ways. For example, fluid can be introduced distally through the elongate body 174A into the priming apparatus 1400. In other embodiments, an inlet, such as a luer, can optionally be formed on a side of the primer housing 1401 to allow for introduction of fluid into the priming apparatus 1400.

A gas permeable membrane can be disposed on a distal end 1404 of the primer housing 1401. The gas permeable membrane can permit air to escape from the primer housing 1401 during priming.

The priming apparatus 1400 also can advantageously be configured to collapse an expandable portion of the catheter assembly 100A. The primer housing 1401 can include a funnel 1415 where the inner diameter of the housing decreases from distal to proximal. The funnel may be gently curved such that relative proximal movement of the impeller housing causes the impeller housing to be collapsed by the funnel 1415. During or after the impeller housing has been fully collapsed, the distal end 170A of the elongate body 174A can be moved distally relative to the collapsed housing. After the impeller housing is fully collapsed and retracted into the elongate body 174A of the sheath assembly, the catheter assembly 100A can be removed from the priming housing 1400 before a percutaneous heart procedure is performed, e.g., before the pump is activated to pump blood. The embodiments disclosed herein may be implemented such that the total time for infusing the system is minimized or reduced. For example, in some implementations, the time to fully infuse the system can be about six minutes or less. In other implementations, the infusate time can be less than 5 minutes, less than 4 minutes, or less than 3 minutes. In yet other implementations, the total time to infuse the system can be about 45 seconds or less. It should be appreciated that lower infusate times can be advantageous for use with cardiovascular patients.

Preparing a Percutaneous Heart Pump for Insertion into the Vasculature

As discussed herein and in the incorporated patent applications, in various embodiments the heart pump is inserted in a less invasive manner, e.g., using techniques that can be employed in a catheter lab.

Prior to insertion of the catheter assembly 100A of the heart pump, various techniques can be used to prepare the system for insertion. For example, as discussed in connection with FIG. 8, the catheter assembly 100A can be primed to remove gas that could be contained therein prior to any method being performed on the patient. This priming technique can be performed by placing a distal portion of the catheter assembly 100A in a priming vessel, such as the apparatus 1400. Thereafter, a media is delivered into the catheter assembly 100A under pressure to displace any potentially harmful matter, e.g., air or other gas, out of the catheter assembly 100A. In one technique, the apparatus 1400 is filled with a biocompatible liquid such as saline. Thereafter, a biocompatible liquid such as saline is caused to flow distally through the catheter assembly 100 to displace air in any of the cavities formed therein, as discussed above. A pressure or flow rate for priming can be provided that is suitable for priming, e.g., a pressure or flow rate that is lower than the operational pressure or flow rate.

In one technique, the biocompatible liquid is pushed under positive pressure from the proximal end through the catheter assembly 100A until all gas is removed from voids therein. One technique for confirming that all gas has been removed is to observe the back-pressure or the current draw of the pump. As discussed above, the priming apparatus 1400 can be configured to permit gas to escape while preventing saline or other biocompatible liquid from escaping. As such, the back-pressure or current draw to maintain a pre-selected flow will change dramatically once all gas has been evacuated.

In another technique, the priming apparatus 1400 can include a source of negative pressure for drawing a biocompatible liquid into the proximal end of the catheter assembly 100A. Applying a negative pressure to the priming apparatus 1400 can have the advantage of permitting the catheter assembly 100A to be primed separate from the pumps that are used during operation of the heart pump. As a result, the priming can be done in parallel with other medical procedures on the patient by an operator that is not directly working on the patient.

In another approach, a positive pressure pump separate from the pump that operates the heart pump can be used to prime under positive pressure applied to the proximal end. Various priming methods may also be expedited by providing a separate inlet for faster filling of the enclosed volume of the priming apparatus 1400.

Collapsing an Expandable Housing of a Fully Primed Catheter Assembly

A further aspect of certain methods of preparing the catheter assembly 100A for insertion into a patient can involve collapsing the impeller housing 116A. The collapsed state of the impeller housing 116A reduces the size, e.g., the crossing profile, of the distal end of the system. This enables a patient to have right, left or right and left side support through a small vessel that is close to the surface of the skin, e.g., using catheter lab-type procedures. As discussed above, in one technique the priming apparatus 1400 has a funnel configuration that has a large diameter at a distal end and a smaller diameter at a proximal end. The funnel gently transitions from the large to the small diameter. The small diameter is close to the collapsed size of the impeller housing 116A and the large diameter is close to or larger than the expanded size of the impeller housing 116A. In one method, after the catheter assembly 100A has been primed, the impeller housing 116A can be collapsed by providing relative movement between the priming apparatus 1400 and the impeller housing 116A. For example, the priming housing 1400 can be held in a fixed position, e.g., by hand, and the catheter assembly 100A can be withdrawn until at least a portion of the impeller assembly 116A is disposed in the small diameter segment of the priming apparatus 1400. Thereafter, the elongate body 174A of the sheath assembly can be advanced over the collapsed impeller assembly 116A.

In another technique, the catheter assembly 100A is held still and the priming apparatus 1400 is slid distally over the impeller assembly 116A to cause the impeller assembly 116A to collapse. Thereafter, relative movement between the elongate body 174A and the impeller assembly 116A can position the distal end 170A of the elongate body 174A over the impeller assembly 116A after the catheter assembly 100A has been fully primed.

Although the inventions herein have been described with reference to particular embodiments, it is to be understood that these embodiments are merely illustrative of the principles and applications of the present inventions. It is therefore to be understood that numerous modifications can be made to the illustrative embodiments and that other arrangements can be devised without departing from the spirit and scope of the present inventions as defined by the appended claims. Thus, it is intended that the present application cover the modifications and variations of these embodiments and their equivalents.

What is claimed is:

1. A fluid handling system, the system comprising:
a housing comprising:
one or more pumps;
a controller configured to operate the pump(s); and
a catheter assembly comprising:
a catheter body having a proximal portion and an operative device at a distal portion; and
an infusion system in fluid communication with the proximal portion of the catheter body, the infusion system comprising a closure member configured to be separate from the housing in a first state and to at least partially secure the infusion system to the housing in a second state, wherein upon engagement of the closure member with the housing in the second state, the infusion system is operably engaged with the pump(s),
wherein the closure member includes an occlusion bed comprising a cavity in the interface body and a tube segment disposed at least partially in the cavity of the occlusion bed,
wherein in the second state, a first pump of the one or more pumps compresses the tube segment against the occlusion bed.

2. The system of claim 1, wherein the housing comprises an aperture, and wherein the closure member engages with the housing when a portion of the closure member is inserted into the aperture.

3. The system of claim 2, wherein the closure member is configured to substantially secure the infusion system to the housing in a third state.

4. The system of claim 3, wherein the closure member is configured to substantially secure the infusion system to the housing when the closure member is rotated relative to the housing.

5. The system of claim 3, wherein the housing comprises a disengagement member, the disengagement member configured to move the closure member from the third state to the second state such that the closure member partially secures the infusion system to the housing.

6. The system of claim 1, wherein upon engagement of the closure member with the housing in the second state, an electrical connection is formed between the housing and an electrical component of the closure member.

7. The system of claim 6, wherein the electrical connection is formed substantially at the same time that the infusion system becomes operably engaged with the pump(s).

8. The system of claim 6, wherein the catheter assembly further comprises a motor assembly in electrical communication with the electrical component of the closure member.

9. The system of claim 6, wherein the catheter assembly further comprises one or more sensors in electrical communication with the electrical component of the closure member.

10. The system of claim 1, wherein the infusion system comprises:
a waste line in fluid communication with the catheter body and configured to convey waste fluid out of the catheter assembly; and
a first infusate line in fluid communication with the catheter body and configured to supply fluid into the catheter assembly.

11. The system of claim 10, wherein the catheter assembly further comprises an elongate body, the catheter body disposed within the elongate body, and wherein the infusion system comprises a second infusate line in fluid communication with the elongate body.

12. The system of claim 11, wherein the second infusate line is configured to supply fluid between the elongate body and the catheter body.

13. A removable interface member for a fluid handling system, the interface member comprising:
an interface body sized and shaped to be inserted into an interface aperture of a console housing;
an electrical component disposed on the interface body;
an occlusion bed disposed on the interface body, the occlusion bed comprising a cavity in the interface body; and
a tube segment disposed on the interface body at least partially in the cavity of the occlusion bed,
wherein the interface body is dimensioned such that when the interface body is inserted into the interface aperture of the console housing, a pump in the console housing is operably engaged with the tube segment and the occlusion bed to compress the tube Segment against the occlusion bed, and an electrical interconnect in the console housing is electrically coupled with the electrical component on the interface body.

14. The removable interface of claim 13, further comprising a locking mechanism such that when a portion of the interface body is rotated relative to the interface aperture, the interface body is securely coupled to the console housing.

15. The removable interface of claim 14, wherein the interface body further comprises a rotatable cap, a protrusion, and a locking aperture sized and shaped to receive at least a portion of the protrusion, the locking mechanism comprising an internal cam that rotates with the cap, wherein when the cap is rotated, the internal cam presses the protrusion through the locking aperture and into a groove formed in the console housing.

16. The removable interface of claim 13, wherein the tube segment comprises an arcuate shape.

17. The removable interface of claim 16, wherein the tube segment generally conforms to the occlusion bed.

18. The removable interface of claim 13, further comprising a second occlusion bed and a second tube segment disposed at least partially in the second occlusion bed.

19. The removable interface of claim 18, wherein the first tube segment is in fluid communication with a fluid supply line and the second tube segment is in fluid communication with a fluid waste line.

20. The removable interface of claim 13, wherein the pump is operably engaged with the tube segment and the occlusion bed when one or more rollers of the pump compresses the tube segment against the occlusion bed.

21. The removable interface of claim 13, wherein, when the interface body is inserted into the interface aperture of the console housing, the pump becomes operably engaged with the tube segment and occlusion bed substantially simultaneously with the electrical interconnect electrically coupling with the electrical component.

22. The removable interface of claim 13, further comprising one or more sensors coupled to the electrical component.

23. A method for operably coupling an infusion system to a console housing, the method comprising:
    positioning an interface body of the infusion system in an interface aperture of the console housing, the interface body comprising an occlusion bed comprising a cavity in the interface body, a tube segment mounted on the interface body at least partially in the cavity of the occlusion bed, and an electrical component; and
    inserting the interface body through the interface aperture until a pump roller of the console housing compresses the tube segment against the occlusion bed and until an electrical interconnect of the console housing is electrically coupled to the electrical component of the interface body.

24. The method of claim 23, further comprising rotating an endpiece of the interface body relative to the interface aperture to secure the interface body to the console housing.

25. The method of claim 24, wherein rotating the endpiece comprises rotating the endpiece about an axis substantially perpendicular to the interface aperture.

26. The method of claim 24, further comprising activating a disengagement member to mechanically release the interface body from the console housing.

27. The method of claim 23, wherein the pump roller compresses the tube segment against the occlusion bed and the electrical interconnect is electrically coupled to the electrical component substantially simultaneously.

* * * * *